United States Patent
Kozicki et al.

(10) Patent No.: US 9,449,355 B2
(45) Date of Patent: Sep. 20, 2016

(54) METHODS AND SYSTEMS FOR FACILITATING ACCESS BY A PATIENT TO ACTIONABLE TASKS ASSOCIATED WITH A CHRONIC CARE PLAN

(71) Applicants: Cellco Partnership, Basking Ridge, NJ (US); Verizon Patent and Licensing Inc., Arlington, VA (US)

(72) Inventors: Scott Kozicki, Franklin, TN (US); Arthur W. Lane, III, Nashville, TN (US); Donald H. Relyea, Dallas, TX (US); Anil K. Solleti, Irving, TX (US)

(73) Assignees: Verizon Patent and Licensing Inc., Basking Ridge, NJ (US); Cellco Partnership, Basking Ridge, NJ (US)

( * ) Notice: Subject to any disclaimer, the term of this patent is extended or adjusted under 35 U.S.C. 154(b) by 340 days.

(21) Appl. No.: 13/854,079

(22) Filed: Mar. 30, 2013

(65) Prior Publication Data
US 2014/0156292 A1    Jun. 5, 2014

Related U.S. Application Data

(60) Provisional application No. 61/732,177, filed on Nov. 30, 2012.

(51) Int. Cl.
| | |
|---|---|
| *G06Q 10/00* | (2012.01) |
| *G06Q 50/00* | (2012.01) |
| *G06Q 50/22* | (2012.01) |
| *G06Q 10/10* | (2012.01) |
| *G06Q 30/06* | (2012.01) |
| *G06F 19/00* | (2011.01) |

(52) U.S. Cl.
CPC .......... *G06Q 50/22* (2013.01); *G06F 19/3418* (2013.01); *G06Q 10/10* (2013.01); *G06Q 30/0631* (2013.01); *G06F 19/363* (2013.01)

(58) Field of Classification Search
CPC .. G06Q 50/22; G06Q 10/10; G06Q 30/0631; G06F 19/3418; G06F 19/363
See application file for complete search history.

(56) References Cited

U.S. PATENT DOCUMENTS

| | | | |
|---|---|---|---|
| 6,039,688 A | 3/2000 | Douglas et al. | |
| 6,957,395 B1* | 10/2005 | Jobs | G06F 3/0481 715/700 |
| 7,260,480 B1* | 8/2007 | Brown et al. | 702/19 |
| 8,479,107 B2* | 7/2013 | Vainio | G06F 3/0488 715/762 |
| 2011/0184250 A1* | 7/2011 | Schmidt | G06Q 10/00 600/300 |

OTHER PUBLICATIONS

Non-Final Office Action received in U.S. Appl. No. 13/854,060 dated Jan. 14, 2015.
Final Office Action received in U.S. Appl. No. 13/854,060 dated Jun. 23, 2015.
Advisory Action received in U.S. Appl. No. 13/854,060 dated Sep. 3, 2015.
"Google patents search", Google patents search, Jan. 8, 2015.

* cited by examiner

*Primary Examiner* — Michelle L Le

(57) ABSTRACT

An exemplary method includes a chronic care solutions provider system 1) maintaining data representative of a chronic care plan for a patient with a chronic medical condition, 2) receiving data representative of a biometric reading acquired by a biometric device associated with the patient, 3) generating a plurality of actionable tasks based on the biometric reading and in accordance with the chronic care plan, and 4) concurrently presenting, within a patient portal accessible by the patient, a plurality of graphical task cards each representative of a distinct actionable task included in the plurality of actionable tasks. Corresponding methods and systems are also disclosed.

14 Claims, 21 Drawing Sheets

Practitioner Portal

| Members | Library | Welcome Dr. Chao \| Sign Out |

Blood Pressure, Systolic Ranges for Sherry Stevens.

Associated Plans: Hypertension Management

| Ranges | Start Range | End Range | Send Alert | Message |
|---|---|---|---|---|
| Low | 60 | 90 | ☑ | Call 911 immediately, your blood pressure is extrem... |
| Low Normal | 91 | 99 | ☐ | |
| Normal | 100 | 120 | ☐ | |
| Above | 121 | 139 | ☐ | |
| High | 140 | 170 | ☑ | Contact your doctor to discuss your blood pressure. |
| Critical | 171 | 999 | ☑ | Call 911 immediately, your blood pressure is danger... |

Submit

Feedback          In case of emergency, Call 911

Fig. 17

METHODS AND SYSTEMS FOR FACILITATING ACCESS BY A PATIENT TO ACTIONABLE TASKS ASSOCIATED WITH A CHRONIC CARE PLAN

RELATED APPLICATIONS

The present application claims priority under 35 U.S.C. §119(e) to U.S. Provisional Patent Application No. 61/732,177, filed Nov. 30, 2012. The contents of the provisional patent application are hereby incorporated by reference in their entirety.

BACKGROUND INFORMATION

Chronic medical conditions, such as diabetes, heart failure, chronic obstructive pulmonary disease, and coronary artery disease, cause about seventy percent of deaths and result in well over a trillion dollars in health care spending each year in the United States alone. In addition to the direct costs in health care, chronic medical conditions are a significant burden to the economy, through limitations in daily activities, lost productivity, and employee absenteeism.

Conventional chronic care techniques often involve prescribing a regimen that a chronic care patient is supposed to follow in between follow-up visits with a health care practitioner (e.g., a doctor or other chronic care provider). Unfortunately, many patients fail to follow these regimens because the health care practitioner is unable to constantly monitor and encourage them in between the follow-up visits. As a result, their chronic medical conditions worsen over time, thereby increasing the cost of caring for them (e.g., in the form of frequent emergency room visits) and inhibiting their ability to live a healthy and productive life.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 5-17 illustrate exemplary interfaces according to principles described herein.

DETAILED DESCRIPTION OF PREFERRED EMBODIMENTS

Methods and systems for facilitating access by a patient to actionable tasks associated with a chronic care plan are described herein. For example, as will be described below, a chronic care solutions provider system may 1) maintain data representative of a chronic care plan for a patient with a chronic medical condition, 2) receive data representative of a biometric reading acquired by a biometric device associated with the patient, 3) generate a plurality of actionable tasks based on the biometric reading and in accordance with the chronic care plan, the actionable tasks configured to assist the patient in managing the chronic medical condition, and 4) concurrently present, within a patient portal accessible by the patient, a plurality of graphical task cards each representative of a distinct actionable task included in the plurality of actionable tasks.

As will be described in more detail below, the graphical task cards may allow the patient to readily ascertain what the actionable tasks are and how he or she may perform the actionable tasks. Moreover, the graphical task cards may be presented in a manner that encourages the patient to interact with and complete the actionable tasks. In this manner, patients may more efficiently, effectively, and/or consistently manage their chronic medical conditions compared with conventional chronic care techniques. This, in turn, may prevent costly emergency room visits, enable the patient to lead a healthy and productive life, and/or reduce the overall cost of health care for everyone.

Figure 1:
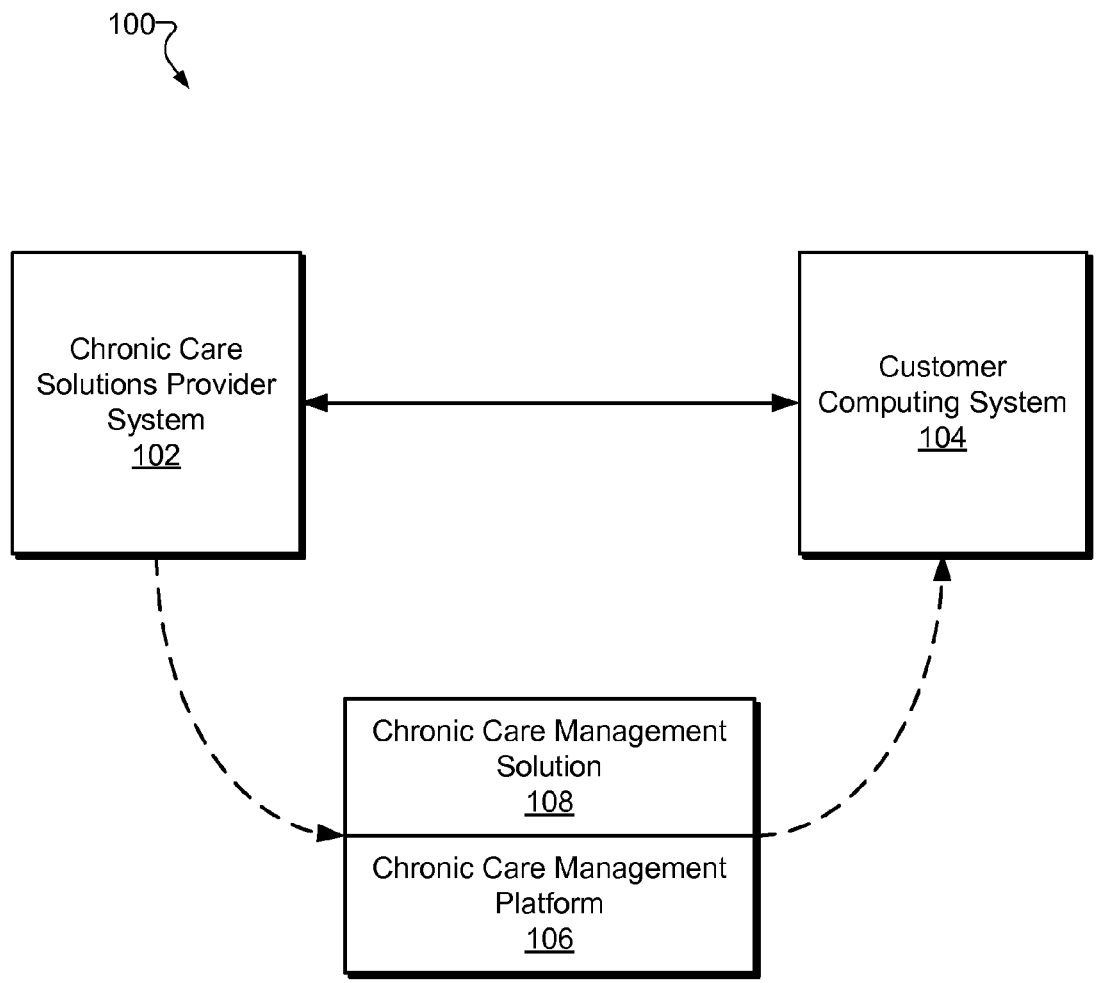
FIG. 1 illustrates an exemplary configuration in which a chronic care solutions provider system is communicatively coupled to a customer computing system according to principles described herein.

FIG. 1 illustrates an exemplary configuration 100 in which a chronic care solutions provider system 102 is communicatively coupled to a customer computing system 104. As illustrated by the dashed lines in FIG. 1 and as will be described in more detail below, chronic care solutions provider system 102 may provide a chronic care platform 106 upon which a chronic care solution 108 may be built for one or more customers associated with customer computing system 104.

Chronic care solutions provider system 102 may be implemented by one or more appropriately configured computing devices (e.g., one or more server devices) and associated with (e.g., owned by, operated by, and/or managed by) a chronic care solutions provider. For example, chronic care solutions provider system 102 may be associated with one or more entities involved in providing a chronic care solution to a customer. To illustrate, chronic care solutions provider system 102 may be associated with a first entity that provides chronic care platform 106 and a second entity that provides chronic care solution 108, a single entity that provides both chronic care platform 106 and chronic care solution 108, and/or any other entity or combination of entities involved in providing chronic care platform 106 and chronic care solution 108 as may serve a particular implementation.

Customer computing system 104 may be associated with (e.g., owned by, operated by, and/or managed by) customers of the chronic care solutions provider and/or users of the chronic care solutions provided by the chronic care solutions provider. For example, customer computing system 104 may be associated with one or more patients with one or more chronic medical conditions, one or more health care practitioners, one or more chronic care solution administrators, one or more health insurance companies, one or more health care practitioner staffing agencies, and/or any other user and/or entity as may serve a particular implementation.

In some examples, chronic care solution 108 may comprise an abstraction of one or more high-level, customer-visible chronic care services ("customer services") provided by the chronic care solutions provider as part of the chronic care solution 108. Such chronic care services may include, but are not limited to, portal services, remote monitoring services, e-prescribing services, payment services, virtual consultation services, etc.

Chronic care platform 106 may comprise an abstraction of one or more lower-level services ("platform services") that support and/or perform the customer services of chronic care solution 108. Platform services may include platform-level services provided by chronic care solutions provider system 102 as part of chronic care platform 106 and that may support, underlie, and/or perform one or more customer services of chronic care solution 108 provided on top of chronic care platform. For example, platform services may include, without limitation, access services, messaging services, biometric device provisioning and fulfillment services, communication services, support services, data transport services, etc.

Various customer and platform services are described in more detail in co-pending U.S. patent application Ser. No. 13/854,060, filed the same day as the present application, and entitled "Methods and Systems for Facilitating Chronic Care of a Patient with a Chronic Medical Condition," the contents of which are incorporated herein by reference in their entirety.

Figure 2:
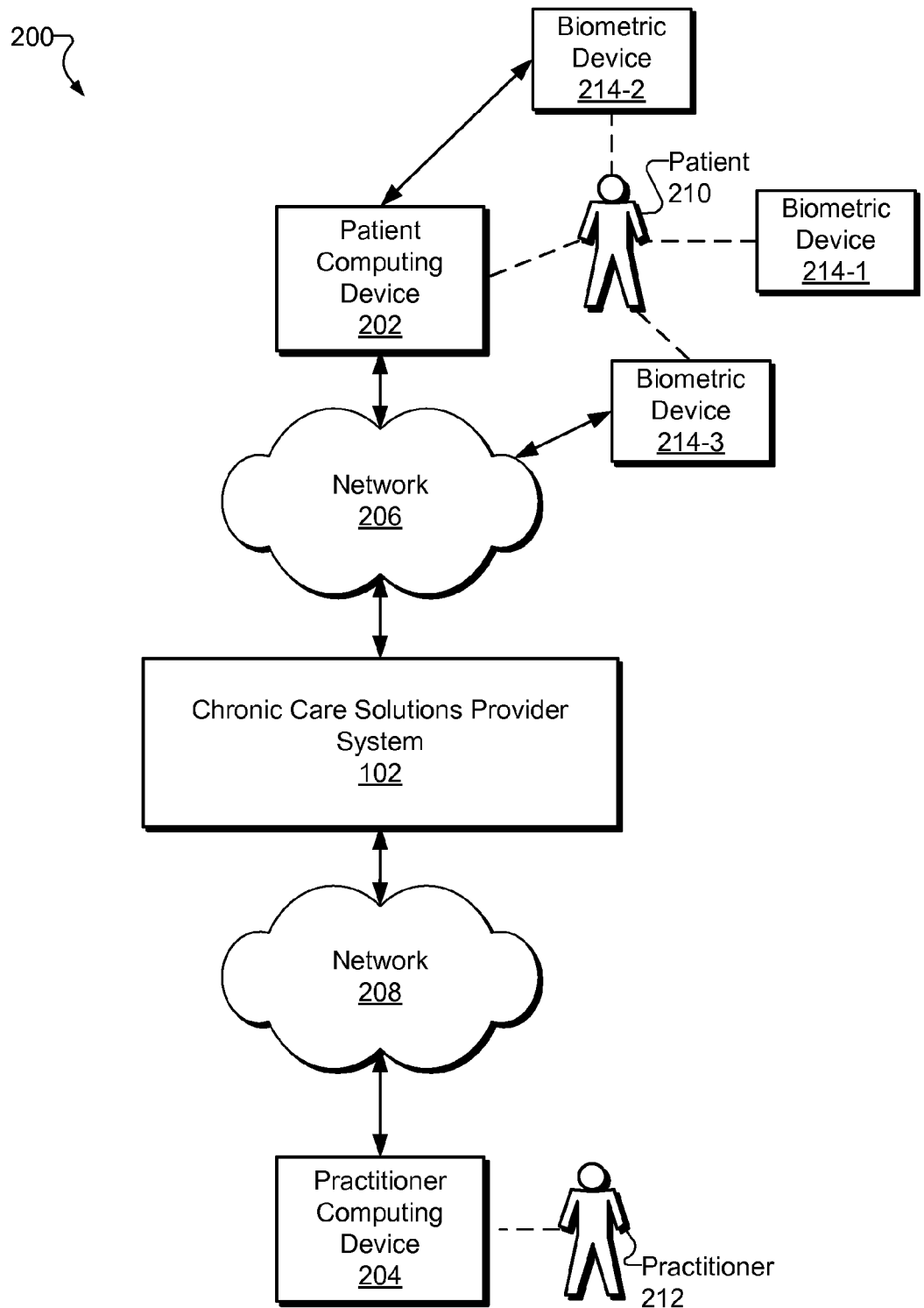
FIG. 2 illustrates an exemplary implementation of the configuration shown in FIG. 1 according to principles described herein.

FIG. 2 illustrates an exemplary implementation 200 of the configuration 100 shown in FIG. 1. As shown, implementation 200 may include a patient computing device 202 and a practitioner computing device 204 each communicatively coupled to chronic care solutions provider system 102 by way of a network (e.g., network 206 and network 208). In some examples, patient computing device 202 and practitioner computing device 204 may implement customer computing system 104.

As shown, patient computing device 202 may be associated with (i.e., used by) a patient 210. Patient 210 may include any person with a chronic medical condition (i.e., a chronic care patient) and who uses patient computing device 202 to avail himself or herself of the chronic care services described herein. Exemplary chronic medical conditions that patient 210 may have include, but are not limited to, diabetes, heart disease (e.g., heart failure, chronic obstructive pulmonary disease, coronary artery disease, etc.), obesity, and/or any other long-term illness, disease, or condition that may require chronic care (i.e., long-term medical care).

Likewise, practitioner computing device 204 may be associated with (i.e., used by) a health care practitioner 212. As used herein, a health care practitioner may include a physician, a physician assistant, a nurse, a dietitian, a therapist, and/or any other chronic care giver or provider.

Patient computing device 202 may be implemented by a mobile device (e.g., a mobile phone, a tablet computer, a laptop computer, etc.), a personal computer, and/or any other suitable computing device that may be configured to access a patient portal provided by chronic care solutions provider system 102. For example, patient computing device 202 may be implemented by a computing device configured to execute and/or otherwise access an application (e.g., a web application or a mobile application) configured to facilitate access by the patient to the chronic care services described herein.

Likewise, practitioner computing device 204 may be implemented by a mobile device (e.g., a mobile phone, a tablet computer, a laptop computer, etc.), a personal computer, and/or any other suitable computing device that may be configured to access a practitioner portal provided by chronic care solutions provider system 102. For example, practitioner computing device 204 may be implemented by a computing device configured to execute and/or otherwise access an application (e.g., a web application or a mobile application) configured to facilitate access by the practitioner to the chronic care services described herein.

It will be recognized that although a single patient computing device 202 and a single practitioner computing device 204 are shown in FIG. 2, any number of patient computing devices and practitioner computing devices may be communicatively coupled to chronic care solutions provider system 102 as may serve a particular implementation. Additional computing devices used by other types of patients (e.g., chronic care solution administrators, etc.) may also be communicatively coupled to chronic care solutions provider system 102.

As shown, patient computing device 202 may communicate with chronic care solutions provider system 102 by way of a network 206. Likewise, practitioner computing device 204 may communicate with chronic care solutions provider system 102 by way of a network 208. Networks 206 and 208 may each include one or more wireless networks, cellular networks (e.g., 3G, 4G, or long term evolution ("LTE") networks), carrier-specific networks, broadband networks, closed media networks, cable networks, satellite networks, the Internet, intranets, wide area networks, local area networks, public networks, private networks, optical fiber networks, and/or any other networks or combination of networks capable of carrying data and communications signals between patient computing device 202 and chronic care solutions provider system 102 and/or between practitioner computing device 204 and chronic care solutions provider system 102. While networks 206 and 208 are shown to be separate networks in FIG. 2 (e.g., network 206 may include one or more telecommunication carrier networks and network 208 may include the Internet), it will be recognized that, in some examples, networks 206 and 208 may alternatively be a single network.

Patient computing device 202, practitioner computing device 204, and chronic care solutions provider system 102 may communicate using any communication technologies suitable for transporting data, including known communication devices, media, and protocols supportive of remote or local data communications. Examples of such communication technologies include, but are not limited to, data transmission media, communications devices (e.g., network devices such as routers, switches, etc.), Transmission Control Protocol ("TCP"), Internet Protocol ("IP"), Hypertext Transfer Protocol ("HTTP"), Hypertext Transfer Protocol Secure ("HTTPS"), Session Initiation Protocol ("SIP"), Ethernet, and any other suitable communications technologies, devices, media, and protocols, including any of those disclosed herein.

As further illustrated in FIG. 2, patient 210 may utilize one or more biometric devices 214 (e.g., biometric devices 214-1 through 214-3) to acquire biometric readings associated with patient 210. As used herein, a "biometric reading" refers to any measurement of one or more biometrics (i.e., one or more health characteristics) of a patient.

Biometric devices 214 may include any suitable device configured to measure one or more biometrics of patient 210. Exemplary biometric devices 214 that may be used in accordance with the methods and systems described herein include, but are not limited to, a glucometer configured to measure blood glucose level of patient 210, a blood pressure monitor configured to measure a blood pressure of patient 210, a weight scale configured to measure a weight of patient 210, and a pulse oximeter configured to measure the level of oxygen saturation in the patient's blood. Some types of biometric devices 214 (e.g., a pulse oximeter) may be configured to continuously monitor a particular biometric of patient 210. Other types of biometric devices 214 (e.g., a weight scale) may be configured to measure a particular biometric of patient 210 only in response to a specific action performed by patient 210 (e.g., when patient 210 steps on the weight scale).

In some examples, as will be described below, it may be desirable for chronic care solutions provider system 102 to process data representative of the biometric readings acquired by biometric devices 214. To this end, data representative of the biometric readings may be communicated to chronic care solutions provider system 102 in any suitable manner depending on the communication capabilities of the various biometric devices 214 that the patient may use.

For example, biometric device 214-1 does not have any communication capabilities. Hence, patient 210 may utilize biometric device 214-1 to acquire a biometric reading and then manually input data representative of the biometric reading into patient computing device 202, which in turn may provide the data representative of the biometric reading to chronic care solutions provider system 102 by way of network 206.

As another example, biometric device 214-2 may be configured to communicate directly with patient computing device 202. For example, biometric device 214-2 and patient computing device 202 may communicate by way of a wireless communication link (e.g., a local area network connection, Bluetooth, infrared, etc.), a wired communication link, and/or any other communication technology as may serve a particular implementation. Hence, in this example, once patient 210 utilizes biometric device 214-2 to acquire a biometric reading, biometric device 214-2 may transmit data representative of the biometric reading to patient computing device 202, which in turn may provide the data representative of the biometric reading to chronic care solutions provider system 102 by way of network 206.

As yet another example, biometric device 214-3 may include one or more communication components (e.g., a wireless network card, a cellular modem, and/or any other type of communication component) configured to facilitate direct communication with chronic care solutions provider system 102 and/or any other system by way of network 206 (e.g., by way of a Wi-Fi or cellular link). In this manner, biometric device 214-3 may transmit data representative of a biometric reading directly to chronic care solutions provider system 102 by way of network 206. In some alternative examples, biometric device 214-3 may be managed by a third party entity not directly associated with chronic care solutions provider system 102. In these examples, biometric device 214-3 may transmit data representative of the biometric reading to a server or other type of system associated with the third party entity by way of network 206. The third party entity may then forward the data representative of the biometric reading to chronic care solutions provider system 102.

Figure 3:
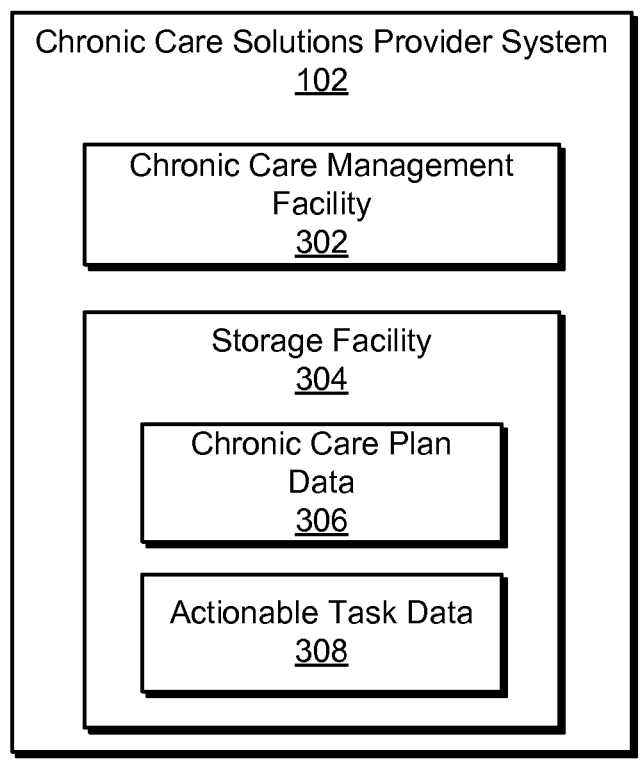
FIG. 3 illustrates exemplary components of a chronic care solutions provider system according to principles described herein.

FIG. 3 illustrates exemplary components of chronic care solutions provider system 102. As mentioned, chronic care solutions provider system 102 may provide a chronic care platform and one or more chronic care solutions by way of the chronic care platform. To this end, chronic care solutions provider system 102 may include a chronic care management facility 302 and a storage facility 304 selectively and communicatively coupled to one another. It will be recognized that although facilities 302 and 304 are shown to be separate facilities in FIG. 3, any of facilities 302-306 may be combined into fewer facilities, such as into a single facility, or divided into more facilities as may serve a particular implementation.

Storage facility 304 may be configured to maintain chronic care plan data 306 representative of one or more chronic care plans associated with one or more patients, actionable task data 308 representative of one or more actionable tasks generated or otherwise used by chronic care management facility 302, and/or any other data generated and/or utilized by chronic care management facility 302 as may serve a particular implementation.

As used herein, a "chronic care plan" represented by chronic care plan data 306 refers to a particular set of guidelines, action items, metrics, and/or regimen that a chronic care patient may follow in order to manage, treat, or otherwise care for a chronic medical condition. For example, a chronic care plan may specify an acceptable range for a particular type of biometric reading associated with a patient, one or more actionable tasks that the patient should perform in order to manage the chronic medical condition, one or more incentives (e.g., reward points) that may be offered to the patient for completing the one or more actionable tasks, a schedule for follow-up visits with a health care practitioner, and/or any other attribute associated with the care of the patient. An "actionable task" represented by actionable task data 308 refers to any task or action item that may be performed by a patient and/or a health care practitioner associated with the patient and that may be configured to assist the patient in managing the chronic medical condition (e.g., by assisting the patient in improving a health characteristic associated with the chronic medical condition as measured by a biometric reading acquired by a biometric device).

Chronic care management facility 302 may be configured to perform one or more chronic care management operations. For example, chronic care management facility 302 may provide various types of portals that may be accessed by various types of users participating in or otherwise associated with a chronic care solution provided by chronic care solutions provider system 102.

Figure 4:
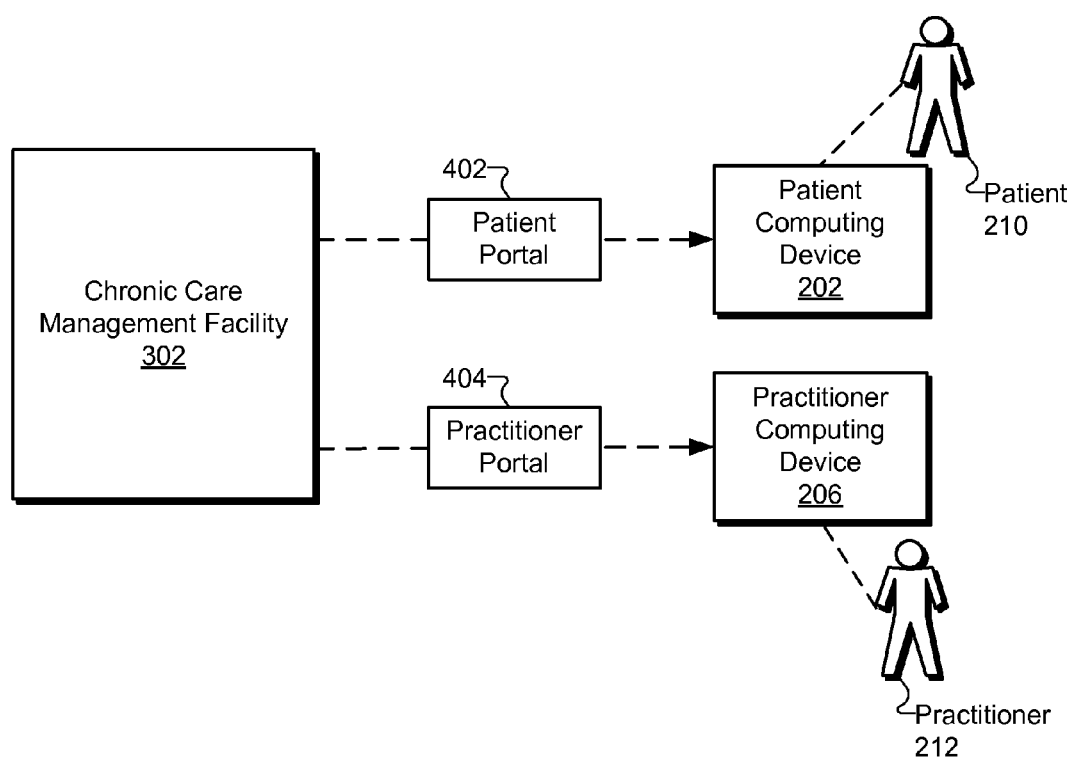
FIG. 4 shows an exemplary configuration in which a chronic care management facility provides a patient portal and a practitioner portal according to principles described herein.

To illustrate, FIG. 4 shows an exemplary configuration in which chronic care management facility 302 provides a patient portal 402 configured to be accessed by patient 210 by way of patient computing device 202 and a practitioner portal 404 configured to be accessed by health care practitioner 212 by way of practitioner computing device 206. Patient portal 402 and practitioner portal 404 may be provided and accessed in any suitable manner. As will be described in more detail below, various types of interfaces may be presented to patient 210 and/or health care practitioner 212 by way of patient portal 402 and practitioner portal 404, respectively. It will be recognized that chronic care management facility 302 may provide additional or alternative types of portals as may serve a particular implementation. For example, chronic care management facility 302 may provide an administrator portal configured to be accessed by a chronic care solution administrator.

Returning to FIG. 3, chronic care management facility 302 may be further configured to perform one or more operations with respect to a chronic care plan associated with the patient. For example, as will be described in more detail below, chronic care management facility 302 may, in accordance with the chronic care plan, provide one or more notifications, process biometric readings, generate actionable tasks, and/or present various types of content by way of a patient portal and/or a practitioner portal for experiencing by the patient and/or a health care practitioner assigned to the patient.

In some examples, a chronic care plan may include a general plan that may be used by a plurality of patients that have the same chronic medical condition. Alternatively, a chronic care plan may be personalized to a particular patient. For example, chronic care management facility 302 may receive (e.g., by way of a practitioner portal) input provided by a health care practitioner representative of one or more attributes of a chronic care plan personalized to a particular patient. In response, chronic care management facility 302 may store data representative of the personalized chronic care plan within storage facility 304 for use by the particular patient.

In some examples, chronic care management facility 302 may provide, in accordance with a chronic care plan associated with a patient, a notification by way of a patient portal for the patient to use a biometric device to acquire a biometric reading associated with the patient. For example, chronic care management facility 302 may provide an alert to the patient for the patient to check her blood glucose level with a glucometer, her blood pressure level with a blood pressure monitor, her weight with a weight scale, her oxygen saturation level with a pulse oximeter, and/or any other biometric reading with any other type of biometric device may serve a particular implementation. Exemplary notifications such as these will be described in more detail below.

In response to the notification, the patient may use a biometric device to acquire a biometric reading. Chronic care management facility 302 may receive data representative of the acquired biometric reading in any suitable manner. For example, as described above, the biometric device may automatically transmit the data representative of the biometric reading to chronic care management facility 302 by way of cellular connection between the biometric device and a network (e.g., network 206) interconnecting the biometric device and chronic care solutions provider system 102.

Alternatively, chronic care management facility 302 may receive the data representative of the biometric reading from a computing device (e.g., patient computing device 202) associated with the patient. For example, the biometric device may automatically transmit the data representative of the biometric reading to the computing device, as described above. The computing device may then forward the data representative of the biometric reading to chronic care management facility 302 (e.g., by way of network 206). Alternatively, the patient may manually input the data representative of the biometric reading into the computing device, which may then forward the data representative of the biometric reading to chronic care management facility 302.

In some examples, chronic care management facility 302 may present the acquired biometric reading within the patient portal and/or within the practitioner portal for experiencing by the patient and/or the health care practitioner. In this manner, the patient and/or health care practitioner may immediately be aware of the biometric reading and take any action deemed necessary in response to the biometric reading.

For example, a health care practitioner may be automatically notified (e.g., by way of an alert presented within a practitioner portal, a text message, etc.) by chronic care management facility 302 that the biometric reading is outside an acceptable range as specified in the chronic care plan associated with the patient. In response, the health care practitioner may contact (e.g., call, initiate a virtual consultation, etc.) the patient to discuss the biometric reading and/or one or more actions that should be taken by the patient to remedy the out of range biometric reading.

In some examples, if the biometric reading is outside an acceptable range as specified in the chronic care plan, chronic care management facility 302 may automatically initiate a consultation between the patient and the health care practitioner. In some examples, the consultation may include a virtual consultation by way of the patient portal and the practitioner portal. Exemplary virtual consultations that may be provided by chronic care management facility 302 are described in more detail in co-pending U.S. patent application Ser. No. 13/854,060, filed the same day as the present application, and entitled "Methods and Systems for Facilitating a Virtual Consultation Between a User and a Health Care Practitioner," the contents of which are incorporated herein by reference in their entirety.

Additionally or alternatively, the health care practitioner may specify one or more actionable tasks that may be performed by the patient in order to improve a health characteristic associated with the medical condition as measured by the biometric reading. In some examples, chronic care management facility 302 may receive input representative of the one or more actionable tasks provided by the health care practitioner by way of the practitioner portal, present a notification of the one or more actionable tasks to the patient by way of the patient portal, and/or update the chronic care plan associated with the patient in accordance with the newly specified one or more actionable tasks. Examples of this will be described in more detail below.

In some examples, chronic care management facility 302 may generate an actionable task based on the biometric reading and in accordance with the chronic care plan. For example, chronic care management facility 302 may determine that the biometric reading is outside an acceptable range specified in the chronic care plan. In response, chronic care management facility 302 may automatically generate an actionable task configured to assist the patient in improving a health characteristic associated with the chronic medical condition as measured by the biometric reading. In this manner, actionable tasks may be dynamically generated in substantially real-time as the patient takes biometric readings, which may allow the patient to more quickly and effectively respond to the biometric reading.

Chronic care management facility 302 may automatically generate an actionable task in any suitable manner. For example, a library of actionable tasks may be maintained by storage facility 304. Chronic care management facility 302 may use the biometric reading to automatically select an appropriate actionable task from the library of actionable tasks. By so doing, the need for a health care practitioner to personally specify the actionable task may be avoided, thereby saving costs associated with the services of the health care practitioner and allowing the patient to more readily respond to an unfavorable biometric reading.

Additionally or alternatively, chronic care management facility 302 may generate an actionable task in response to input provided by a health care practitioner. For example, as described above, chronic care management facility 302 may present the biometric reading to a health care practitioner assigned to the patient. Chronic care management facility 302 may then receive input provided by the health care practitioner in response to the biometric reading and generate the actionable task based on the input provided by the health care practitioner.

In some examples, chronic care management facility 302 may generate an actionable task based on a plurality of biometric readings. For example, a patient may use a particular biometric device to acquire a plurality of biometric readings over the course of a particular time period (e.g., a day, a week, etc.). Chronic care management facility 302 may generate an actionable task based on these biometric readings as a whole. For example, the biometric readings may be indicative of a biometric trend that may not be readily apparent based on a single biometric reading. Hence, chronic care management facility 302 may generate an actionable task that is configured to reverse or otherwise address the biometric trend identified using the plurality of biometric readings.

In some examples, chronic care management facility 302 may generate an actionable task based on biometric readings generated by different biometric devices. For example, chronic care management facility 302 may provide a first notification to the patient by way of the patient portal for the patient to weigh herself using a weight scale. Chronic care management facility 302 may also provide a second notification to the patient by way of the patient portal for the patient to measure her blood glucose level with a glucometer. Chronic care management facility 302 may then generate an actionable task based on the patient's weight and blood glucose level.

Chronic care management facility 302 may be further configured to present an interactive task interface by way of the patient portal. The interactive task interface may be configured to facilitate completion by the patient of one or more actionable tasks generated by chronic care management facility 302. For example, the interactive task interface may include a notification of an actionable task generated in response to a biometric reading and one or more instructions (e.g., step-by-step instructions) regarding how to complete the actionable task. As will be described in more detail below, chronic care management facility 302 may also present other content (e.g., a graphical object representative of progress made by the patient towards one or more goals associated with the chronic care plan and at least one recommendation for managing the chronic medical condition) within the interactive task interface.

In some scenarios, chronic care management facility 302 may generate multiple actionable tasks based on the biometric reading in accordance with the chronic care plan. In these scenarios, chronic care management facility 302 may graphically portray the actionable tasks within the interactive task interface in a manner that allows the patient to readily ascertain what the actionable tasks are and in a manner that encourages the patient to interact with and complete the actionable tasks.

For example, chronic care management facility 302 may concurrently present, within the interactive task interface, a plurality of graphical task cards each representative of a distinct actionable task included in the plurality of actionable tasks. The graphical task cards may be presented in any suitable manner. For example, as will be illustrated below, the graphical task cards may be presented in a staggered stack arrangement such that at least a portion of each of the graphical task cards is visible within the patient portal.

Chronic care management facility 302 may be further configured to detect a completion by the patient of an actionable task and, in response, reward the patient with one or more reward points. In this manner, the patient may be incentivized to work on and complete actionable tasks. In some examples, chronic care patient management facility 302 may present, within the patient portal, an option to redeem the one or more reward points for one or more prizes (e.g., gift cards, massages, items of clothing, and/or any other suitable item as may serve a particular implementation).

Various examples of the methods and systems described herein will now be provided. It will be recognized that the examples provided herein are merely illustrative of the many different implementations that may be realized in accordance with the methods and systems described herein. For example, additional or alternative interfaces to those described below may be presented in accordance with the methods and systems described herein.

Figure 5:
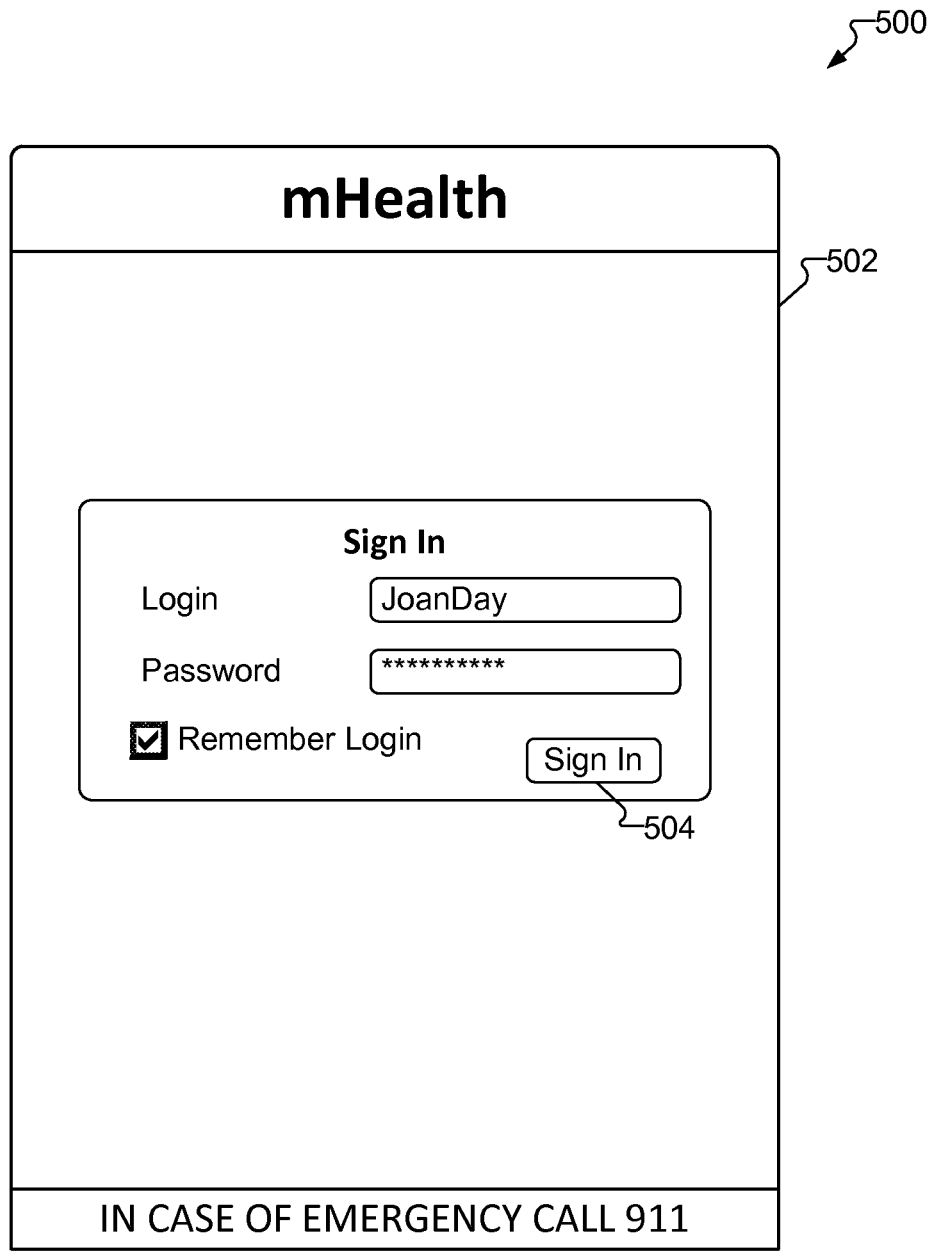

FIG. 5 illustrates an exemplary patient portal 500 that may be provided by chronic care management facility 302 for presentation to a patient (e.g., by way of patient computing device 202). Patient portal 500 may be presented in any suitable manner. For example, patient portal 500 may be presented in the context of a standalone application (e.g., a mobile application), a webpage, and/or in any other manner as may serve a particular implementation. As will be described herein, various interfaces may be presented within patient portal 500 to facilitate management of a chronic medical condition associated with a patient.

As shown, a login interface 502 may be initially presented within patient portal 500. A patient may utilize login interface 502 to access one or more of the chronic care services described herein. For example, as shown, the patient may enter a login ID and password and select a "sign in" option 504. It will be recognized that a patient may alternatively access one or more of the chronic care services described herein in any other manner. For example, a user of a mobile device may simply initiate a mobile application executed by the mobile device to access the chronic care services described herein.

Figure 6:
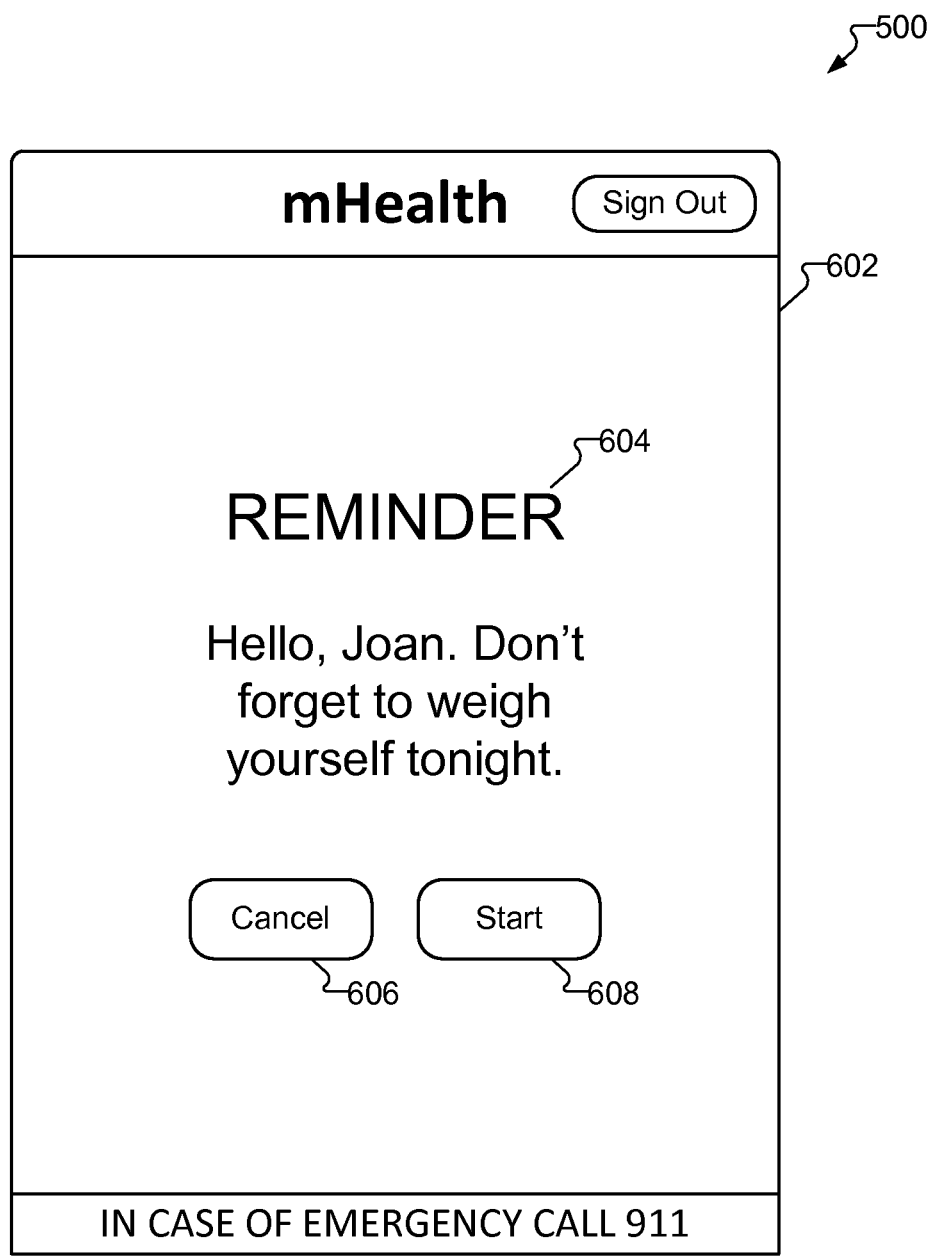

FIG. 6 illustrates an exemplary notification interface 602 that may be presented within patient portal 500 after the patient has logged in using login interface 502. As shown, chronic care management facility 302 may provide, in accordance with a chronic care plan associated with the patient, a notification 604 for presentation within notification interface 602 for the patient to use a biometric device to acquire a biometric reading associated with the patient. In the particular example of FIG. 6, notification 604 is for the patient to weigh herself using a weight scale. It will be recognized that additional or alternative types of notifications may be provided by way of patient portal 500 as may serve a particular implementation.

As shown, the patient may select a "cancel" option 606 to ignore notification 604. Alternatively, the patient may select a "start" option 608 to access an interface configured to facilitate acquisition of the biometric reading.

Figure 7:
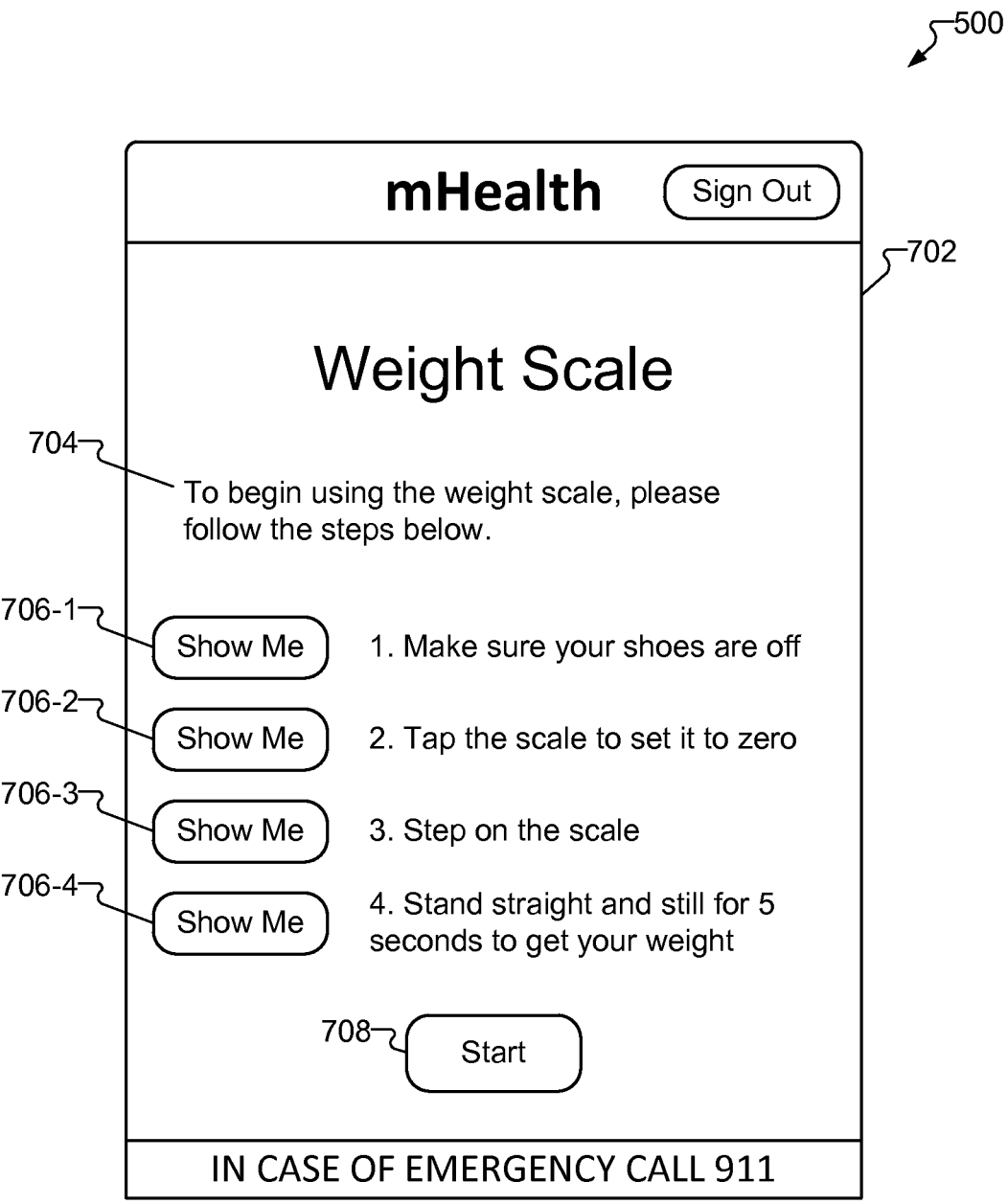

To illustrate, FIG. 7 shows an exemplary instructions interface 702 that may be presented within patient portal 500 in response to the patient selecting the "start" option 608 shown in FIG. 6. As shown, instructions 704 about how to acquire the biometric reading may be provided within instructions interface 702. In this particular example, instructions 704 detail a number of steps that may be taken by the patient in order to weigh herself using a weight scale. As shown, one or more options 706 (e.g., options 706-1 through 706-4) may be selected by the patient in order to access additional content (e.g., video content) that describe in more detail how to perform each of the steps included in instructions 704. For example, in response to the patient selecting option 706-1, chronic care management facility 302 may present, within patient portal 500, a video illustrating how to take one's shoes off. Once the patient is aware of how to use the biometric device to acquire the biometric reading, she may select option 708 to proceed with acquiring the biometric reading.

Figure 8:
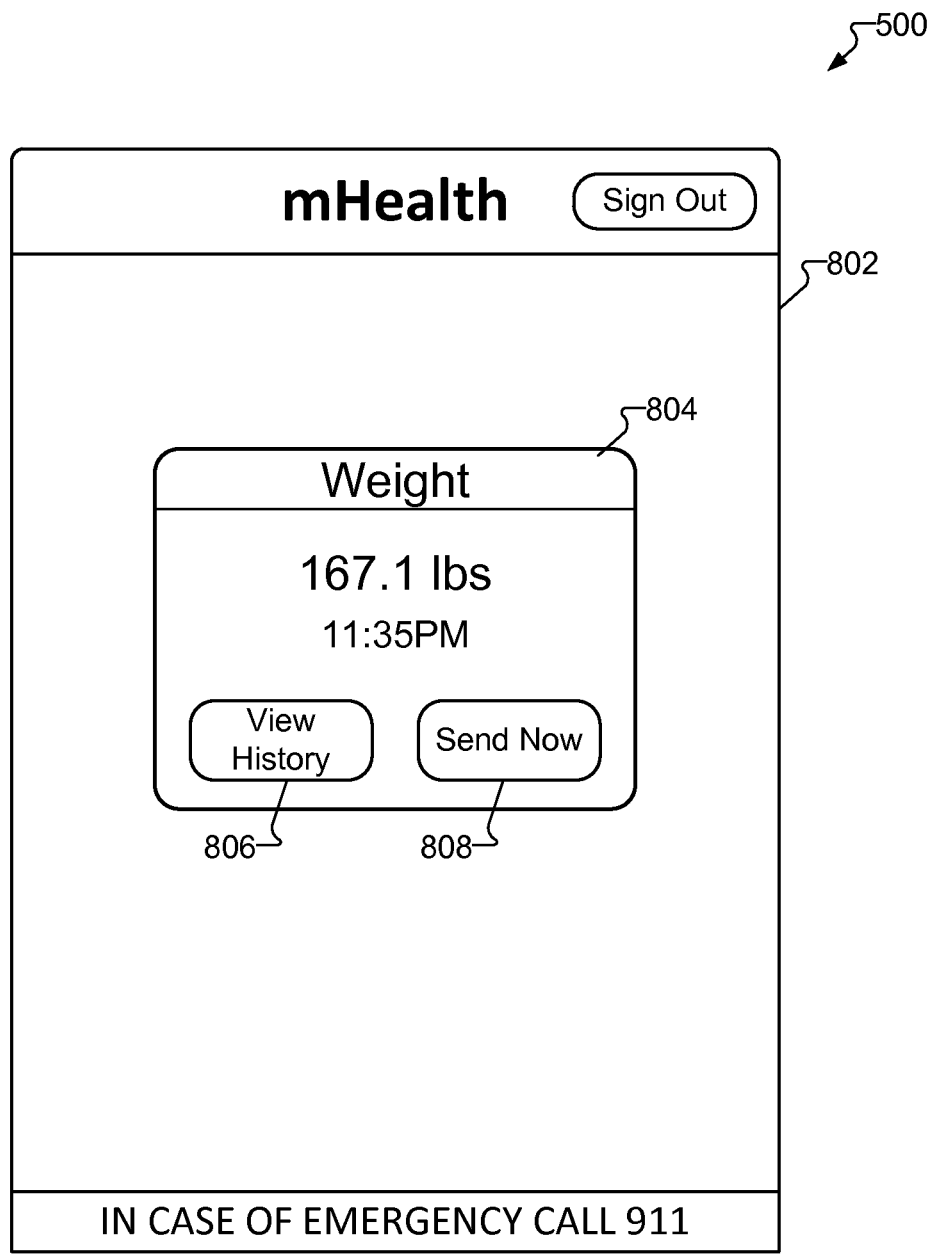

FIG. 8 illustrates an exemplary results interface 802 that may be presented within patient portal 500 in response to the patient using the biometric device to acquire the biometric reading. As shown, a notification 804 may be presented within results interface 802 that includes information representative of the biometric reading. In this particular example, notification 804 shows that the weight scale acquired a biometric reading of 167.1 pounds ("lbs") at 11:35 pm. In this manner, the patient may immediately know the results of the biometric reading.

In some examples, the patient may select a "view history" option 806 to view a log of previously acquired weight measurements. The patient may also select a "send now" option 808 to send data representative of the biometric reading from patient computing device 202 to chronic care solutions provider system 102. Alternatively, as described above, chronic care solutions provider system 102 may receive the data representative of the biometric reading directly from the biometric device (i.e., the weight scale). In this embodiment, the "send now" option 808 may be omitted.

In instances in which the biometric device is not configured to communicate with either patient computing device 202 or chronic care solutions provider system 102, an interface may be presented within patient portal 500 requesting the patient to manually enter data representative of the biometric reading. The patient may then direct patient computing device 202 transmit the data representative of the biometric reading in any suitable manner.

Figure 9:
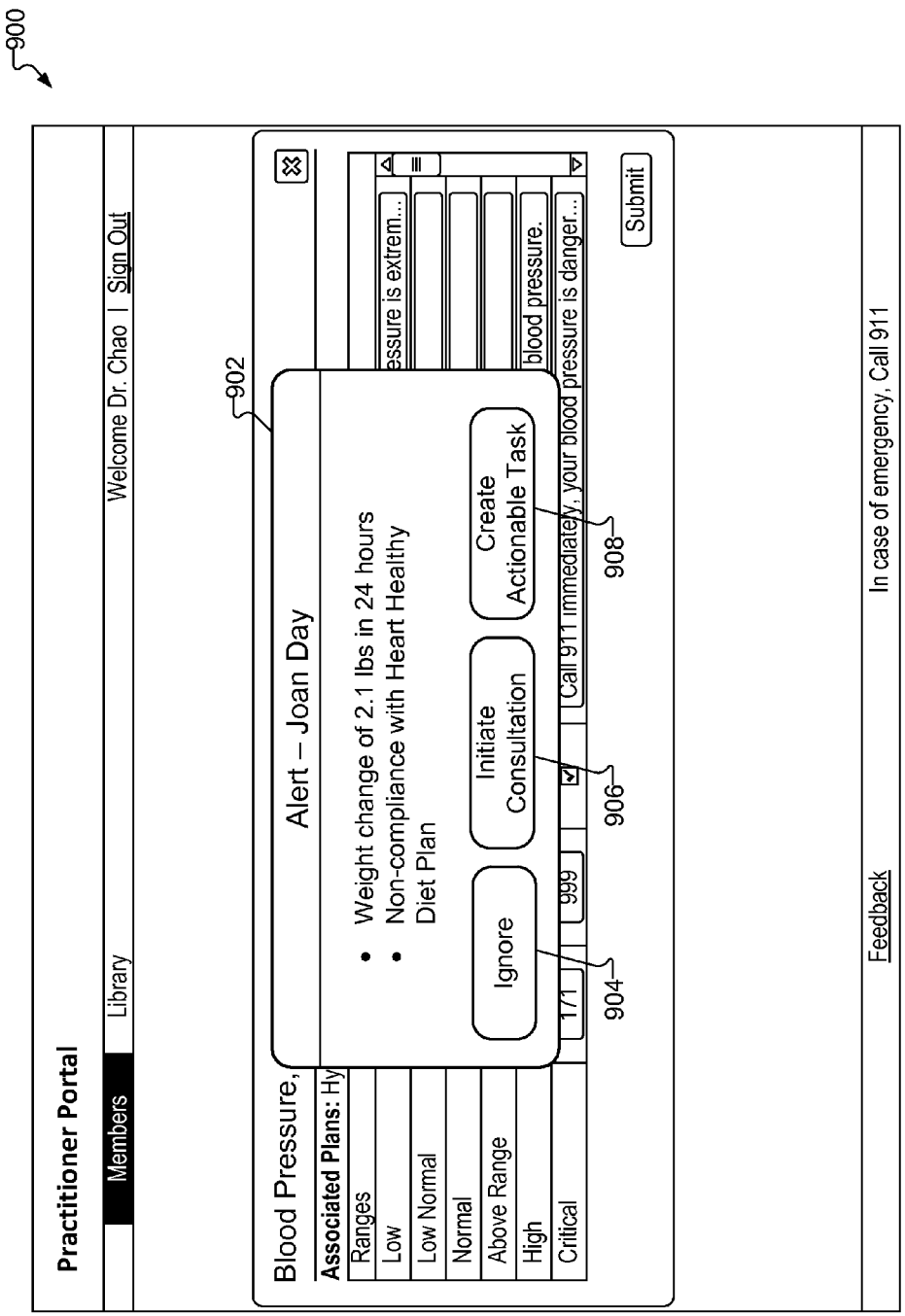

In some examples (e.g., in cases where the biometric reading is outside an acceptable range specified in the chronic care plan), chronic care management facility 302 may notify a health care practitioner assigned to the patient of the biometric reading. For example, FIG. 9 illustrates an exemplary practitioner portal 900 that may be accessed by a health care practitioner assigned to the patient described in connection with FIGS. 5-8. As shown, a notification 902 (i.e., a graphical object representative of an alert) may be presented within practitioner portal 900 in response to chronic care management facility 302 determining that the weight of the patient has deviated outside an acceptable range as specified in the patient's chronic care plan.

In some examples, notification 902 may include one or more options that the health care practitioner may select in order to address and/or ignore the biometric reading. For example, the health care practitioner may select an "ignore" option 904 to ignore the notification.

Alternatively, the health care practitioner may select an "initiate consultation" option 906 to initiate a consultation with the patient. As described above, the consultation may include a virtual consultation by way of patient portal 500 and practitioner portal 900 (e.g., an online video conference, an online audio conference, an online chat session, and or any other form of real-time communication as may serve a particular implementation). Alternatively, the consultation may include a phone call and/or any other type of communication as may serve a particular implementation.

Figure 10:
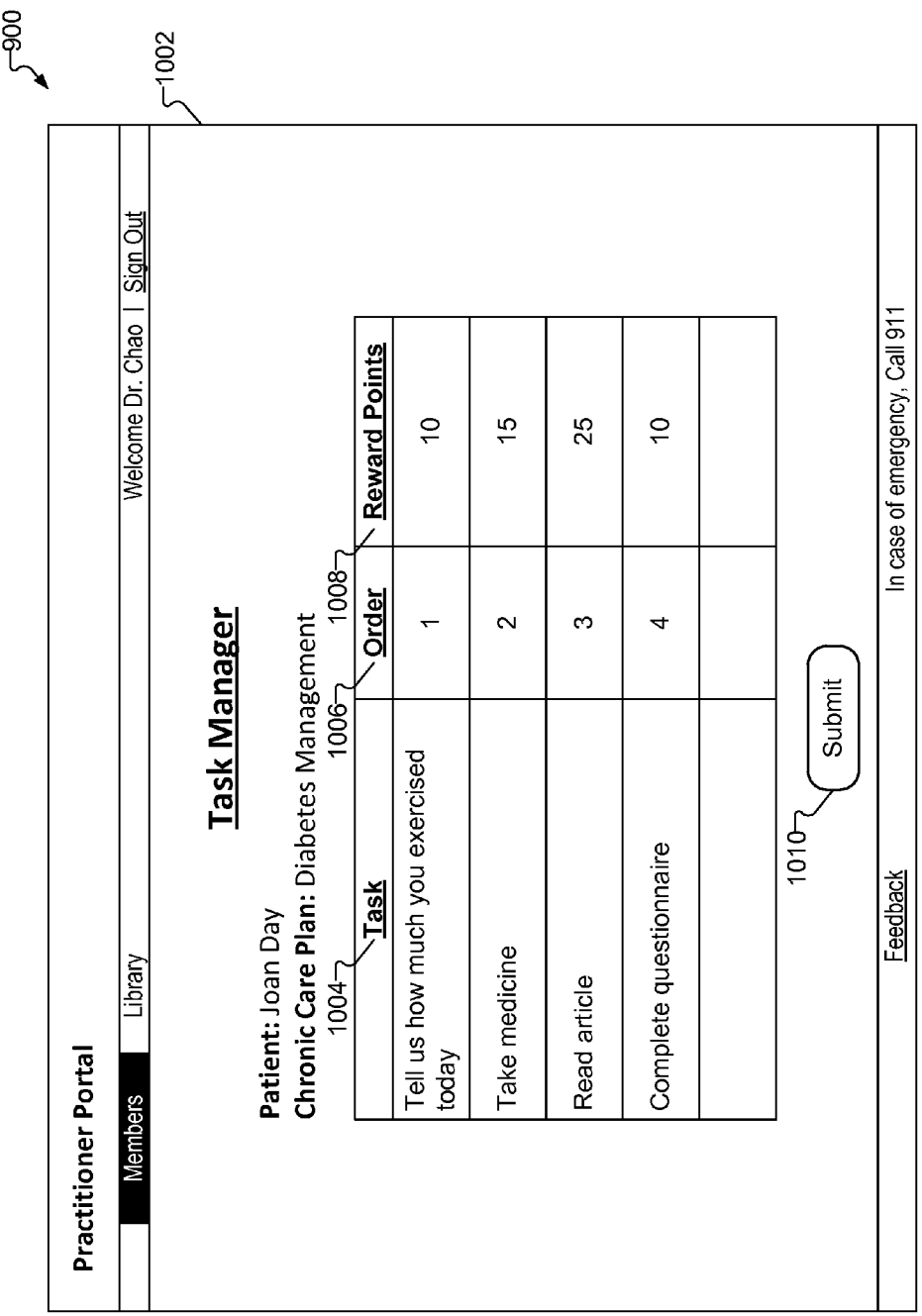

As shown, the health care practitioner may alternatively select a "create actionable task" option 908 to create one or more actionable tasks based on the biometric reading. To illustrate, FIG. 10 shows an exemplary task manager interface 1002 that may be presented within practitioner portal 900 in response to the health care practitioner selecting option 908.

As shown, task manager interface 1002 may provide one or more input fields into which the health care practitioner may enter data representative of one or more actionable tasks and or other types of data associated with the actionable tasks. For example, task manager interface 1002 may include a "task" field column 1004 into which the health care practitioner may enter text descriptive of an actionable task, an "order" field column 1006 into which the health care practitioner may enter a preferred order of completion for various actionable tasks, and a "reward points" field column 1008 into which the health care practitioner may enter a number of reward points that may be awarded to the patient upon completion of the various tasks. To illustrate, FIG. 10 shows that the health care practitioner has created four actionable tasks (e.g., "tell us how much you exercised today," "take medicine," "read article," and "complete questionnaire") and assigned each of the four actionable tasks a particular order number and a particular amount of reward points to the awarded upon completion of the tasks.

Once the health care practitioner has created a desired number of actionable tasks, he or she may select a "submit" option 1010. In response, chronic care management facility 302 may generate the actionable tasks based on the input provided by the health care practitioner.

Alternatively, as described above, chronic care management facility 302 may automatically generate one or more actionable tasks based on the biometric reading. For example, in response to the biometric reading that the patient's weight is outside the acceptable range specified in the patient's chronic care plan, chronic care management facility 302 may automatically select one or more actionable tasks from a library of actionable tasks maintained by storage facility 304.

Figure 11:
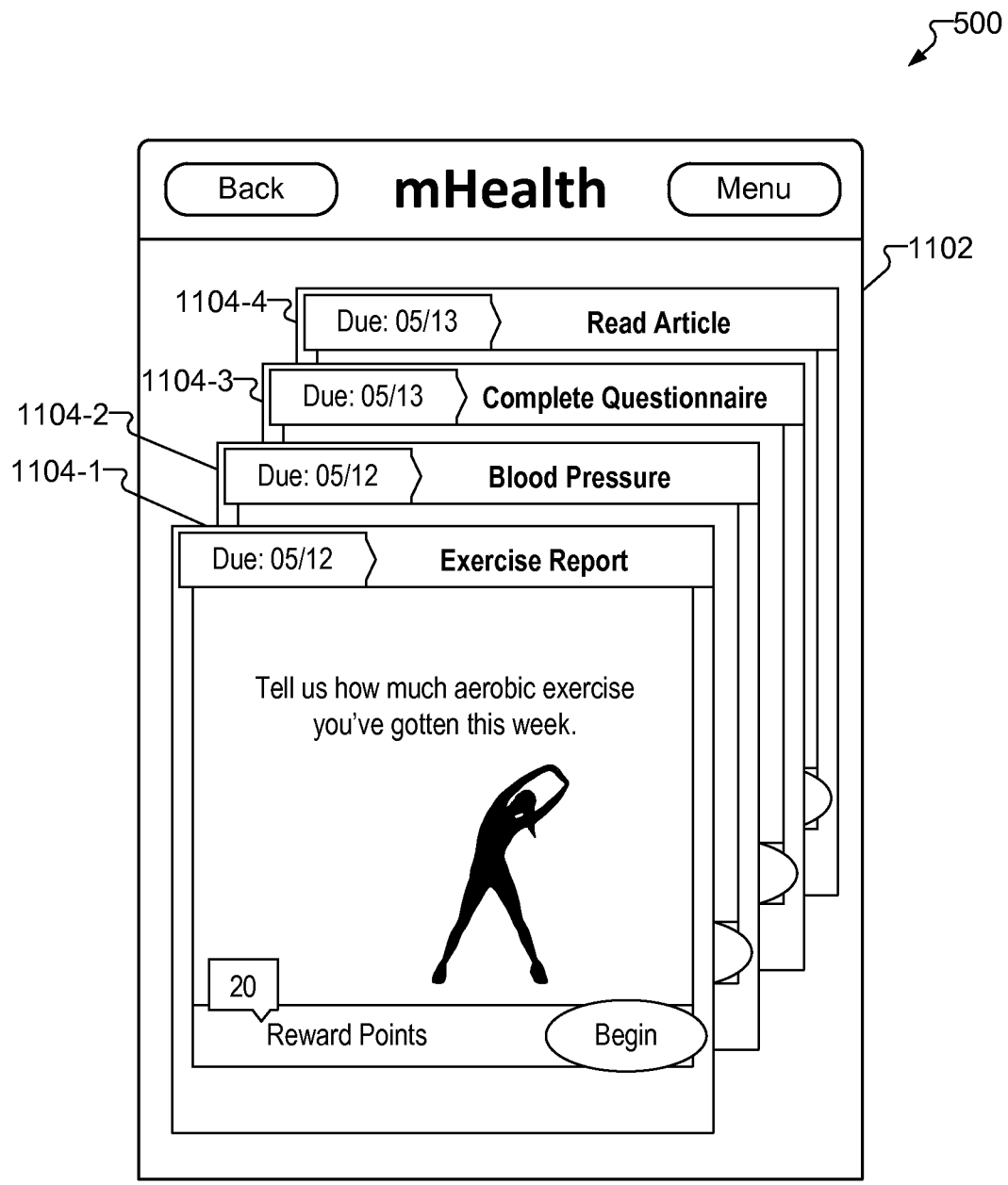

FIG. 11 illustrates an exemplary interactive task interface 1102 that may be presented within patient portal 500 and that may be configured to facilitate completion by the patient of one or more actionable tasks generated in response to an acquisition of the biometric reading associated with the patient.

As shown, a plurality of graphical task cards 1104 (e.g., graphical task cards 1104-1 through 1104-4) each representative of a distinct actionable task included in a plurality of actionable tasks generated in response to the acquisition of the biometric reading may be concurrently presented within interactive task interface 1102. It will be recognized that chronic care management facility 302 may graphically portray the actionable tasks within interactive task interface 1102 in any other suitable manner. For example, chronic care management facility 302 may alternatively graphically portray the actionable tasks as a list of selectable links each configured to facilitate access to additional details about an associated actionable task, a series of non-overlapping graphical objects, and/or in any other manner as may serve a particular implementation.

As shown, graphical task cards 1104 are presented in a staggered stack arrangement such that at least a portion of each of the graphical task cards 1104 is visible within patient portal 500 (i.e., within interactive task interface 1102). In some examples, graphical task cards 1104 may be ordered within the staggered stack arrangement in accordance with an order in which the actionable tasks represented by graphical task cards 1104 are to be completed by the patient. For example, in the example of FIG. 11, the "exercise report" actionable task represented by graphical task card 1104-1 is to be completed first by the patient, followed by the "blood pressure" actionable task, the "complete questionnaire" actionable task, and the "read article" actionable task, represented by graphical task cards 1104-2 through 1104-4, respectively.

In some examples, the patient may interact with graphical task cards 1104 in order to view or otherwise access content presented within each of the graphical task cards 1104. For example, the patient may use one or more touch gestures to shuffle through the graphical task cards 1104. To illustrate, chronic care management facility 302 may detect a touch gesture performed by the patient with respect to a touch screen within which patient portal 500 is displayed. The touch gesture may include any suitable touch gesture, such as a swipe gesture by an object (e.g., a finger, stylus, or other object) in any direction while the object is in contact with the touch screen, a tap gesture by the object, and/or any other suitable touch gesture as may serve a particular implementation. In response to the touch gesture, chronic care management facility 302 may shuffle the graphical task cards 1104 within the staggered stack arrangement.

Figure 12:
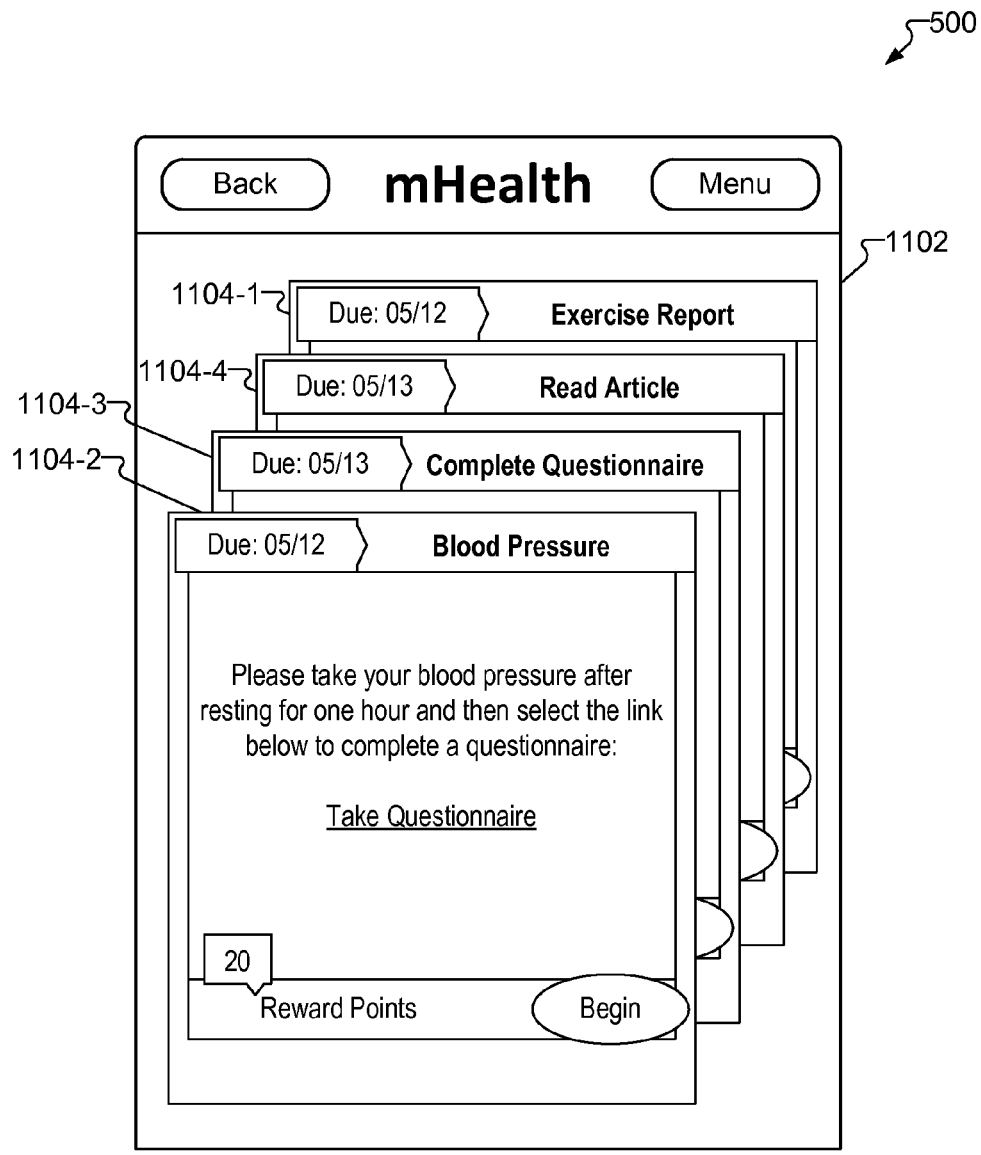

Chronic care management facility 302 may shuffle graphical task cards 1104 in any suitable manner. For example, chronic care management facility 302 may shuffle the graphical task cards 1104 by graphically bringing a graphical task card (e.g., graphical task card 1104-2) located beneath a top of the staggered stack arrangement prior to the touch gesture being performed to being located at the top of the staggered stack arrangement. To illustrate, FIG. 12 shows interactive task interface 1102 after graphical task cards 1104 have been shuffled in response to a touch gesture performed by the patient. As shown, graphical task card 1104-2 has been brought to the top of the staggered stack arrangement and graphical task card 1104-1 has been placed at the bottom of the staggered stack arrangement.

Figure 13:
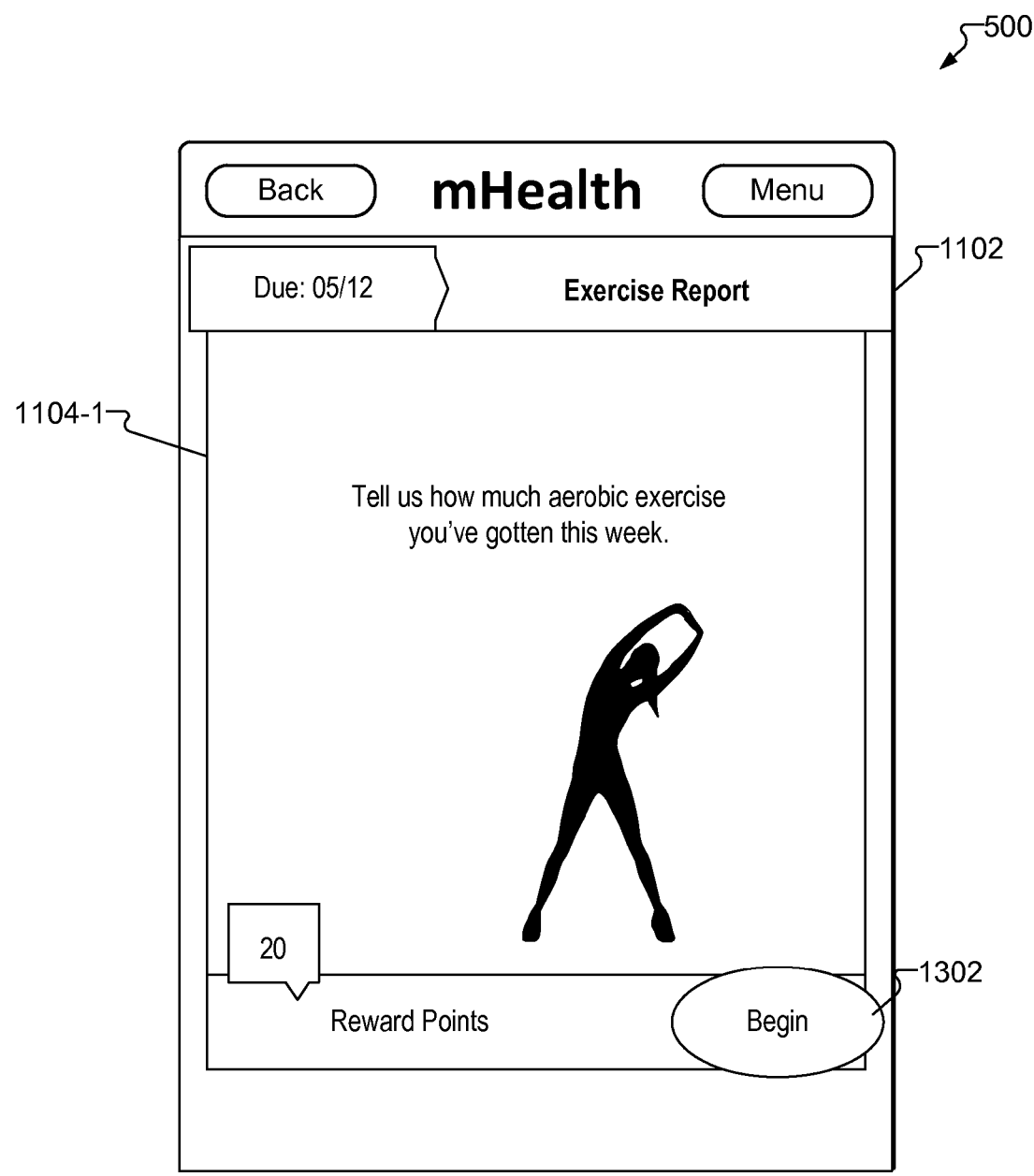

In some examples, each graphical task card 1104 is interactive and configured to facilitate completion by the patient of a corresponding actionable task. For example, the patient may select graphical task card 1104-1 (e.g., by tapping graphical task card 1104-1) to access content associated with and/or complete the actionable task represented by graphical task card 1104-1. In response, chronic care management facility 302 may enlarge the selected graphical task card 1104-1 within patient portal 500. FIG. 13 shows patient portal 500 after graphical task card 1102-1 has been enlarged. As shown, the enlarging may include maximizing a size of graphical task card 1102-1 within patient portal 500 such that the remaining number of graphical task cards (i.e., graphical task cards 1104-2 through 1104-4) are not visible within patient portal 500.

The patient may then select a "begin" option 1302 included within graphical task card 1104-1 in order to complete the actionable task represented by graphical task card 1104-1. It will be recognized that option 1302 may be selected at any time (e.g., before graphical task card 1104-1 has been enlarged).

Figure 14:
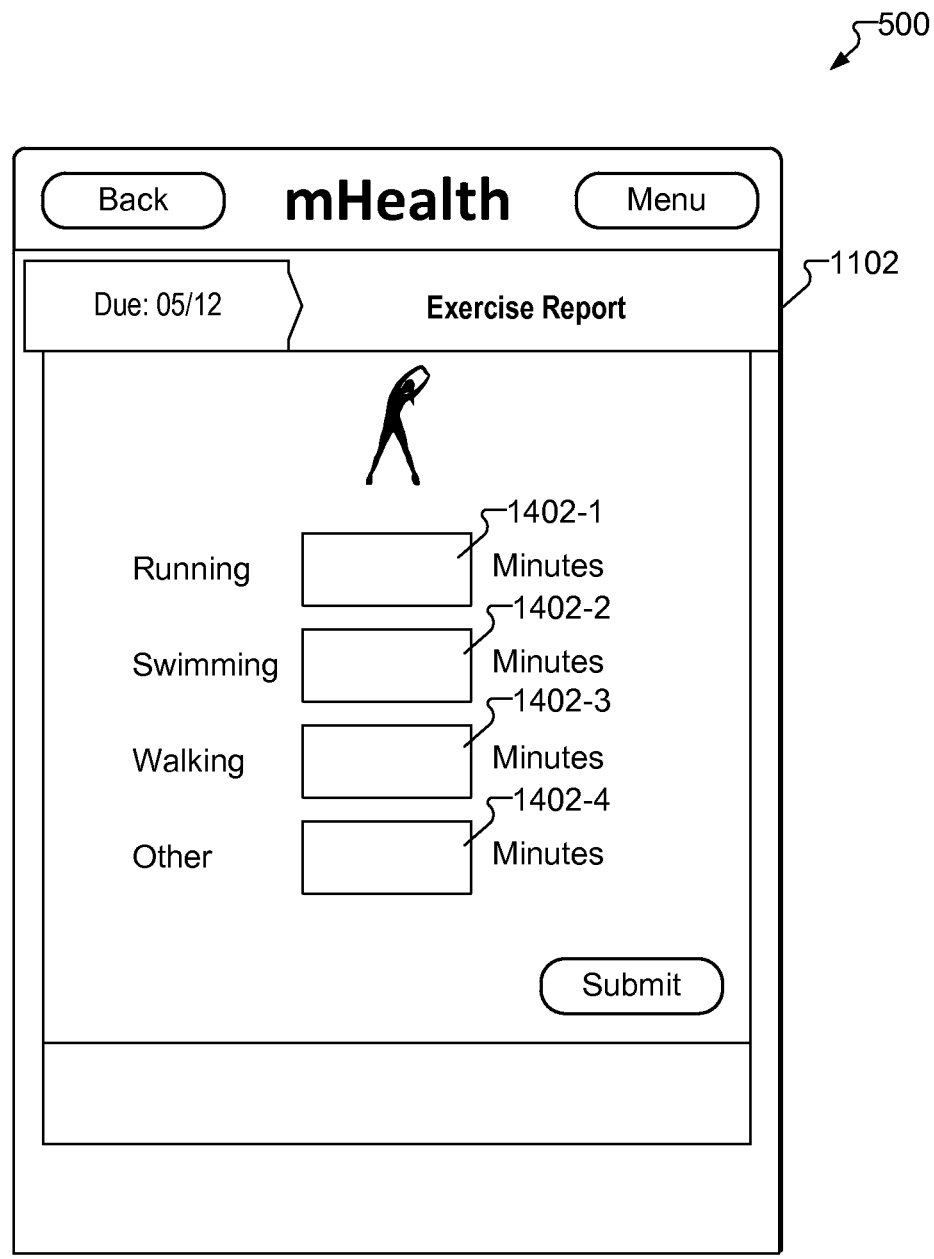

FIG. 14 shows patient portal 500 after option 1302 has been selected by the patient. As shown, a plurality of input fields 1402 (i.e., input fields 1402-1 through 1402-4) may be presented within patient portal 500 and used to complete the actionable task specified by graphical task card 1104-1. It will be recognized that any other content configured to assist the patient in completing the actionable task may be presented within patient portal 500 as may serve a particular implementation.

Figure 15:

FIG. 15 illustrates an exemplary interface 1502 that may be presented within patient portal 500 in response to completion by the patient of an actionable task. As shown, interface 1502 may include a message 1504 congratulating the patient for completing the actionable task. Interface 1502 may include any other content as may serve a particular implementation.

Figure 16:
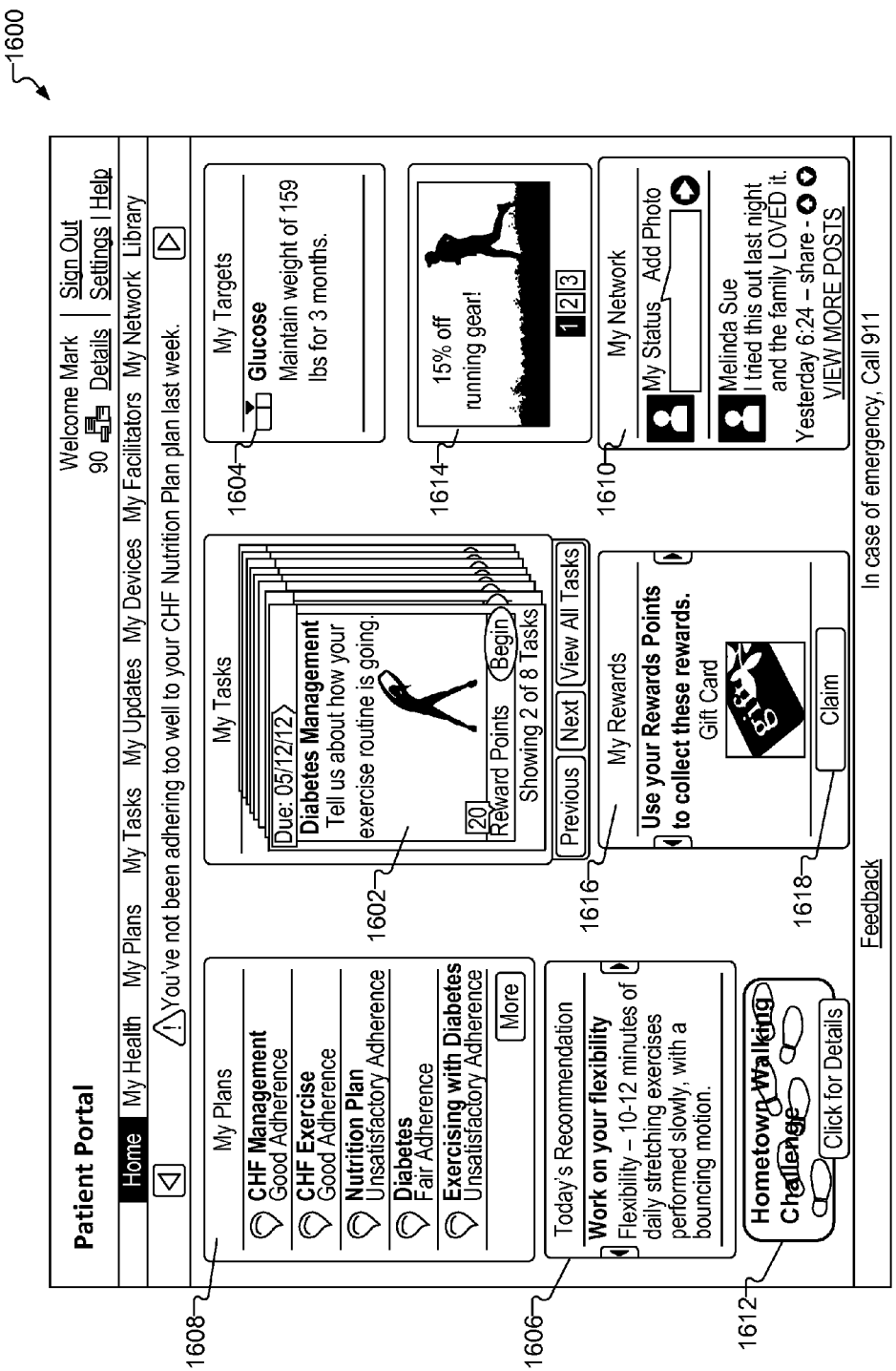

FIG. 16 illustrates another exemplary patient portal 1600 that may be presented to the patient. As shown, patient portal 1600 may include a variety of types of content related to a chronic care plan associated with the patient. For example, chronic care management facility 302 may concurrently present, within patient portal 1600, a plurality of graphical objects 1602 (e.g., graphical task cards) each representative of a distinct actionable task included in a plurality of actionable tasks configured to assist the patient in managing the chronic medical condition, a graphical object 1604 representative of progress made by the patient towards one or more goals associated with the chronic care plan, and at least one recommendation 1606 for managing the chronic medical condition. Patient portal 1600 may further include information 1608 associated with (e.g., descriptive of) one or more chronic care plans associated with the patient, social network content 1610 associated with the patient (e.g., social network posts by other patients with the same chronic medical condition as the patient, and one or more advertisements (e.g., advertisements 1612 and 1614) associated with (e.g., selected in accordance with) the chronic medical condition and one or more biometric readings acquired by the patient.

Each of these types of content may be dynamically updated as the patient takes various biometric readings, completes various actionable tasks, and/or in response to any other factor as may serve a particular implementation. For example, advertisements 1612 and 1614 may be dynamically changed as the patient improves in caring for his or her chronic medical condition (as evidenced by a trend of completed actionable tasks). To illustrate, an advertisement 1612 for a smoking cessation program may be initially presented to the patient by way of patient portal 1600 when the patient first starts accessing the chronic care services described herein. As the patient completes actionable tasks configured to help the patient stop smoking, advertisement 1612 may be updated to include an advertisement for exercise equipment.

As shown, patient portal 1600 may also include rewards content 1616 associated with a rewards program in which the patient is enrolled. As described above, a patient may receive reward points for completing an actionable task and/or for any other reason. In this manner, the patient may be incentivized to access the chronic care services described herein (e.g., by working on and completing actionable tasks). Patient portal 1600 may also include an option 1618 that may be selected to redeem one or more reward points for one or more prizes (e.g., gift cards, massages, items of clothing, and/or any other suitable item as may serve a particular implementation).

In some examples, a chronic care plan may be personalized to a patient. For example, a health care practitioner may define one or more acceptable ranges associated with a biometric reading for inclusion in the chronic care plan. To illustrate, FIG. 17 shows an exemplary biometric reading management interface 1702 that may be presented within practitioner portal 900 and that may be used by a health care practitioner to provide input representative of one or more acceptable ranges associated with a biometric reading for inclusion in the chronic care plan. As shown, the practitioner has specified a number of possible ranges 1704 (e.g., ranges 1704-1 through 1704-6) for a blood pressure reading taken by the patient. As shown, a "low" range 1704-1 is between 60 and 90, a "low normal" range 1704-2 is between 91 and 99, a "normal" range 1704-3 is between 100 and 120, an "above" range 1704-4 is between 121 and 139, a "high" range 1704-5 is between 140 and 170, and a "critical" range 1704-6 is between 171 and 999.

In some examples, one or more of the ranges 1704 defined in biometric reading management interface 1702 may be designated as being "acceptable." For example, in the example of FIG. 17, ranges 1704-2 through 1704-4 are designated as being acceptable (i.e., an alert will not be sent to the health care practitioner and a warning message will not be presented to the patient if a biometric reading falls within any of these ranges). However, if the biometric reading falls within ranges 1704-1, 1704-5, or 1704-6, biometric reading management interface 1702 shows that an alert will be sent to the health care practitioner and a warning message (which, as shown in FIG. 17, may be specified by the health care practitioner) will be presented to the patient by way of the patient portal.

Figure 18:
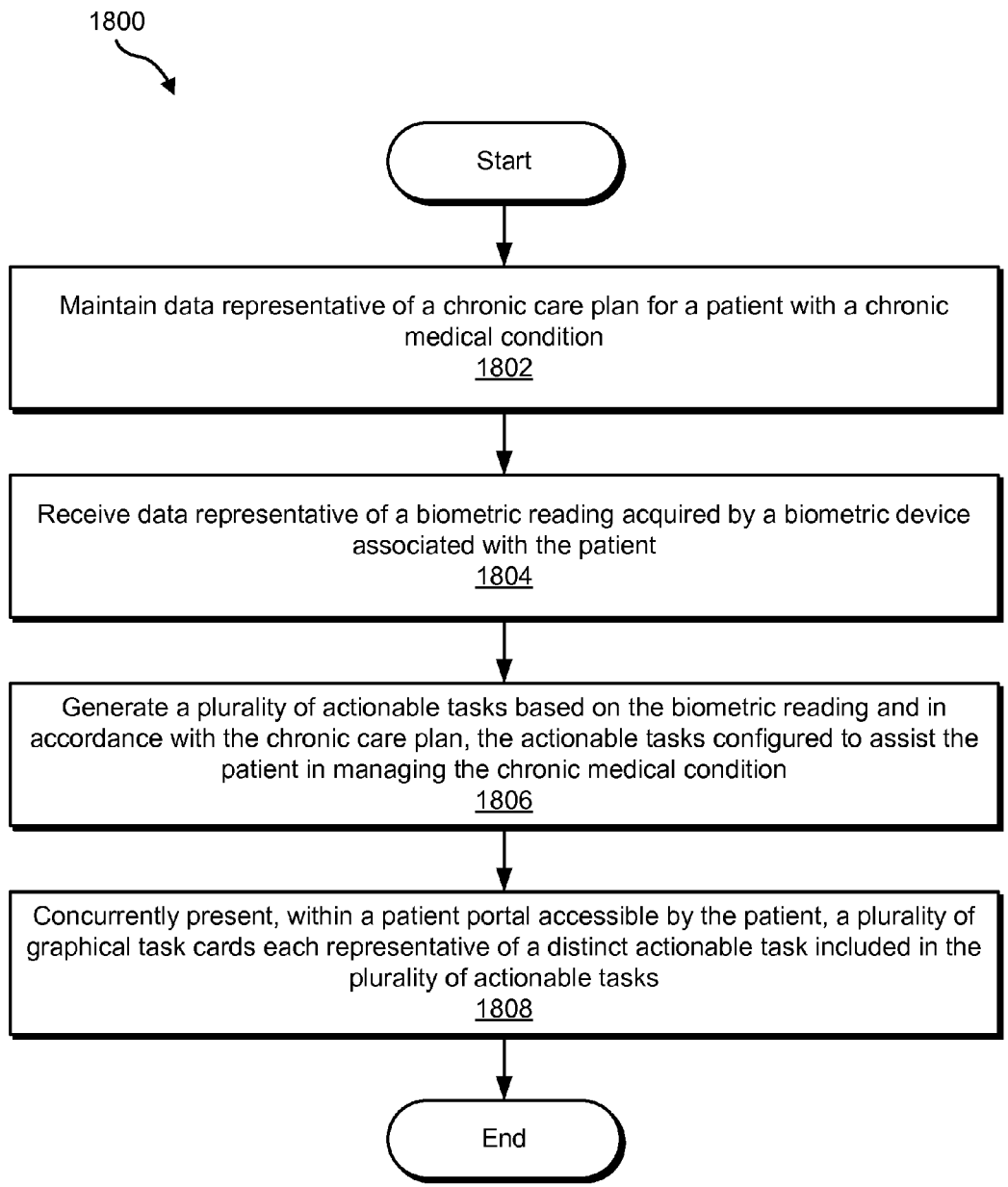
FIG. 18 illustrates an exemplary method of facilitating access by a patient to actionable tasks associated with a chronic care plan according to principles described herein.

FIG. 18 illustrates an exemplary method 1800 of facilitating access by a patient to actionable tasks associated with a chronic care plan. While FIG. 18 illustrates exemplary steps according to one embodiment, other embodiments may omit, add to, reorder, and/or modify any of the steps shown in FIG. 18. One or more of the steps shown in FIG. 18 may be performed by chronic care solutions provider system 102 and/or any implementation thereof.

In step 1802, a chronic care solutions provider system maintains data representative of a chronic care plan for a patient with a chronic medical condition. Step 1802 may be performed in any of the ways described herein.

In step 1804, the chronic care solutions provider system receives data representative of a biometric reading acquired by a biometric device associated with the patient. Step 1804 may be performed in any of the ways described herein.

In step 1806, the chronic care solutions provider system generates a plurality of actionable tasks based on the biometric reading and in accordance with the chronic care plan. As described above, the actionable tasks may be configured to assist the patient in managing the chronic medical condition. Step 1806 may be performed in any of the ways described herein.

In step 1808, the chronic care solutions provider system concurrently presents, within a patient portal accessible by the patient, a plurality of graphical task cards each representative of a distinct actionable task included in the plurality of actionable tasks. Step 1808 may be performed in any of the ways described herein.

Figure 19:
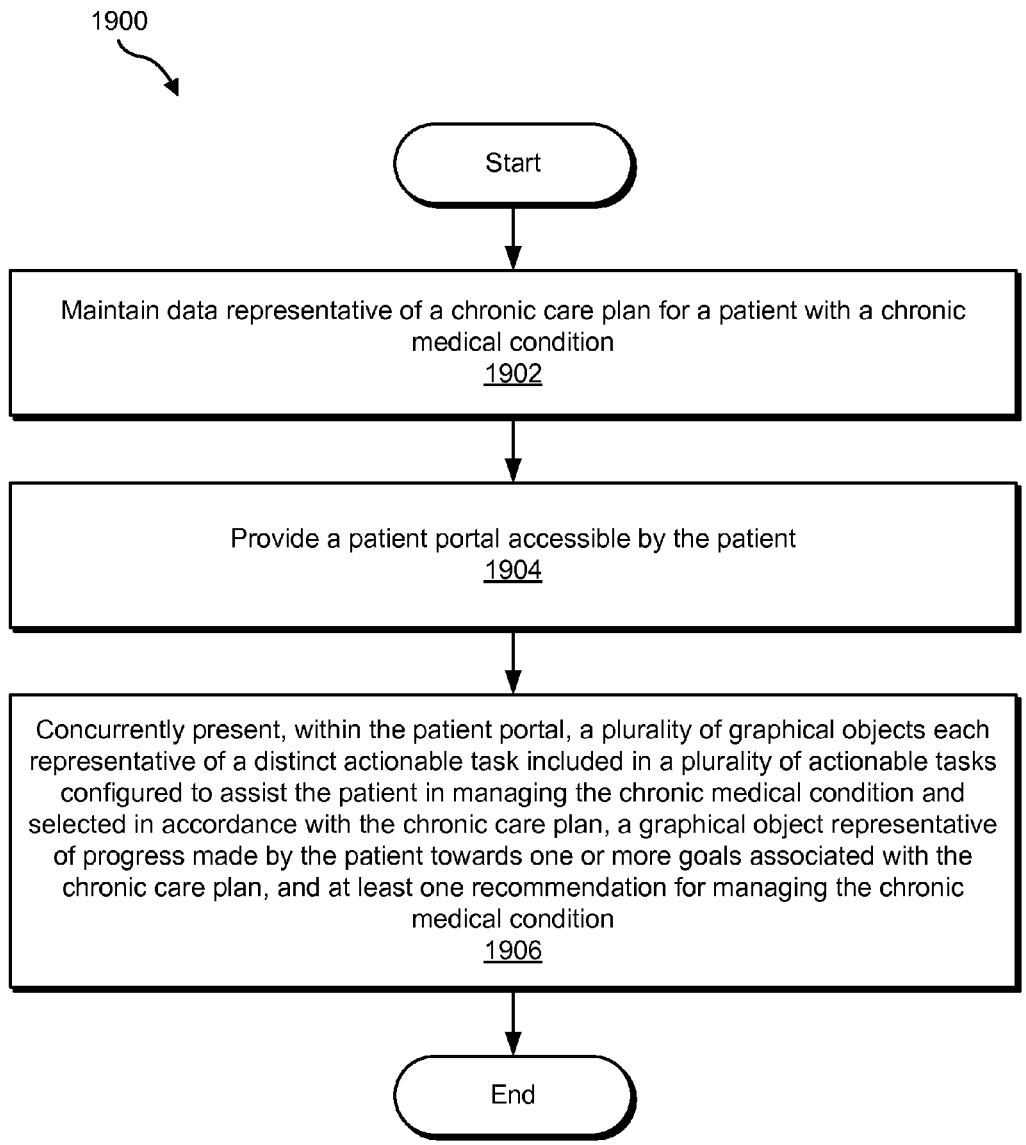
FIG. 19 illustrates another exemplary method of facilitating access by a patient to actionable tasks associated with a chronic care plan according to principles described herein.

FIG. 19 illustrates another exemplary method 1900 of facilitating access by a patient to actionable tasks associated with a chronic care plan. While FIG. 19 illustrates exemplary steps according to one embodiment, other embodiments may omit, add to, reorder, and/or modify any of the steps shown in FIG. 19. One or more of the steps shown in FIG. 19 may be performed by chronic care solutions provider system 102 and/or any implementation thereof.

In step 1902, a chronic care solutions provider system maintains data representative of a chronic care plan for a patient with a chronic medical condition. Step 1902 may be performed in any of the ways described herein.

In step 1904, the chronic care solutions provider system provides a patient portal accessible by the patient. Step 1904 may be performed in any of the ways described herein.

In step 1906, the chronic care solutions provider system concurrently presents, within the patient portal, a plurality of graphical objects each representative of a distinct actionable task included in a plurality of actionable tasks configured to assist the patient in managing the chronic medical condition and selected in accordance with the chronic care plan, a graphical object representative of progress made by the patient towards one or more goals associated with the chronic care plan, and at least one recommendation for managing the chronic medical condition. Step 1906 may be performed in any of the ways described herein.

Figure 20:
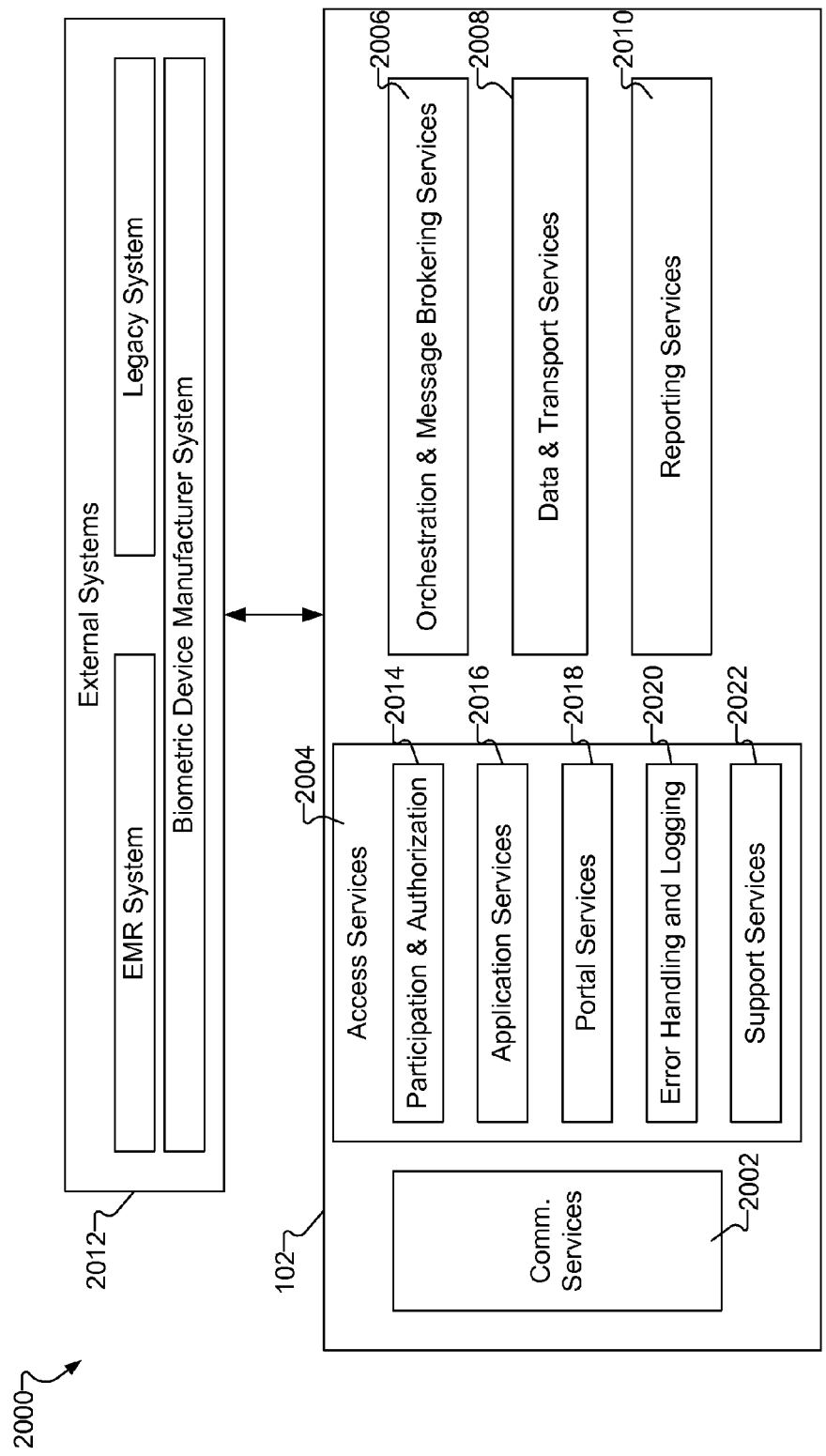
FIG. 20 illustrates an exemplary implementation of the chronic care solutions provider system shown in FIG. 3 according to principles described herein.

FIG. 20 illustrates an exemplary implementation 2000 of chronic care solutions provider system 102. In particular, implementation 2000 shows various services (i.e., platform services and/or customer services) that may be provided by chronic care solutions provider system 102. For example, as shown, chronic care solutions provider system 102 may provide communication services 2002, access services 2004, orchestration and message brokering services 2006, data and transport services 2008, and reporting services 2010. Additional or alternative platform services may be provided as may serve a particular implementation. Together, the various platform services illustrated in FIG. 20 provide a chronic care platform (e.g., chronic care platform 106) upon which one or more chronic care solutions may be built.

Communication services 2002 may facilitate communication by chronic care solutions provider system 102 with various external devices and/or systems. For example, communication services 2002 may provide a communication services layer by which chronic care solutions provider system 102 may communicate with one or more patient computing devices (e.g., patient computing device 202) and one or more practitioner computing devices (e.g., practitioner computing device 204).

Communication services 2002 may additionally or alternatively facilitate communication by chronic care solutions provider system 102 with external systems 2012. In some examples, external systems 2012 may be associated with (e.g., managed by) one or more entities not associated with chronic care solutions provider system 102. As shown, such external systems 2012 may include an electronic medical record ("EMR") system, one or more legacy systems, and one or more biometric device manufacturer systems configured to provide, maintain, or otherwise manage biometric devices used in connection with the methods and systems described herein.

Access services 2004 may be configured to facilitate access by patients, health care practitioners, administrators, and/or other types of users to the chronic care solutions provided by chronic care solutions provider system 102. For example, access services 2004 may provide participation and authorization services 2014, application services 2016, portal services 2018, error handling and logging services 2020, and support services 2022.

Participation and authorization services 2014 may include access management services configured to facilitate secure collaboration with external systems (e.g., external systems 2012) with regulatory mandates and enable comprehensive security for applications, web services, and data. Participation and authorization services 2014 may also include authentication services configured to validate that a particular patient is allowed to access one or more chronic care services (e.g., by verifying login IDs and passwords). Participation and authorization services 2014 may also include registration services configured to provide a registration process that may be used by a patient and/or health care practitioner to register for chronic care services.

Application services 2016 may include scheduling services configured to facilitate scheduling by health care practitioners, diagnosis and assessment services configured to facilitate remote monitoring by health care practitioners of patients, payment services configured to allow patients to securely submit payments online, and virtual consultation services configured to facilitate virtual consultations between patients and health care practitioners.

Portal services 2018 may include administration services configured to allow an administrator to manage the various portals provided by chronic care solutions provider system 102, e-prescribing services configured to allow a health care practitioner to provide a patient with online prescriptions, patient portal services configured to facilitate presentation of a patient portal to a patient, and practitioner portal services configured to facilitate presentation of a practitioner portal to a health care practitioner.

Error handling and logging services 2020 may include one or more services configured to handle and/or log faults that may occur within any of the other services provided by chronic care solutions provider system 102. Error handling and logging services 2020 may be further configured to provide one or more options for auditing the faults.

Support services 2022 may be configured to provide support (e.g., customer support) for the various services provided by chronic care solutions provider system 102.

Orchestration and message brokering services 2006 may be configured to provide one or more workflow management services. Orchestration and message brokering services 2006 may be further configured to provide message routing and brokering services. For example, the recipients of patient data (i.e., external systems 2012) may require data in a specific health care standard format. This service ensures appropriate message transformation, message validation and routing for each of the 2012 external systems. Orchestration and message brokering services 2006 may be further configured to provide message parser services.

Data and transport services 2008 may be configured to provide a secure database and data warehouse for runtime as well as complex analytics and reporting services. In some examples, the underlying database for storing data may include a relational data (e.g. MS SQL, Oracle, etc.) warehouse.

Reporting services 2010 may be configured to facilitate creation and generation of various reports associated with the chronic care services provided by chronic care solutions provider system 102. For example, reporting services 2010 process data acquired by chronic care solutions provider system 102 and generate and present one or more reports based on the data.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 21:
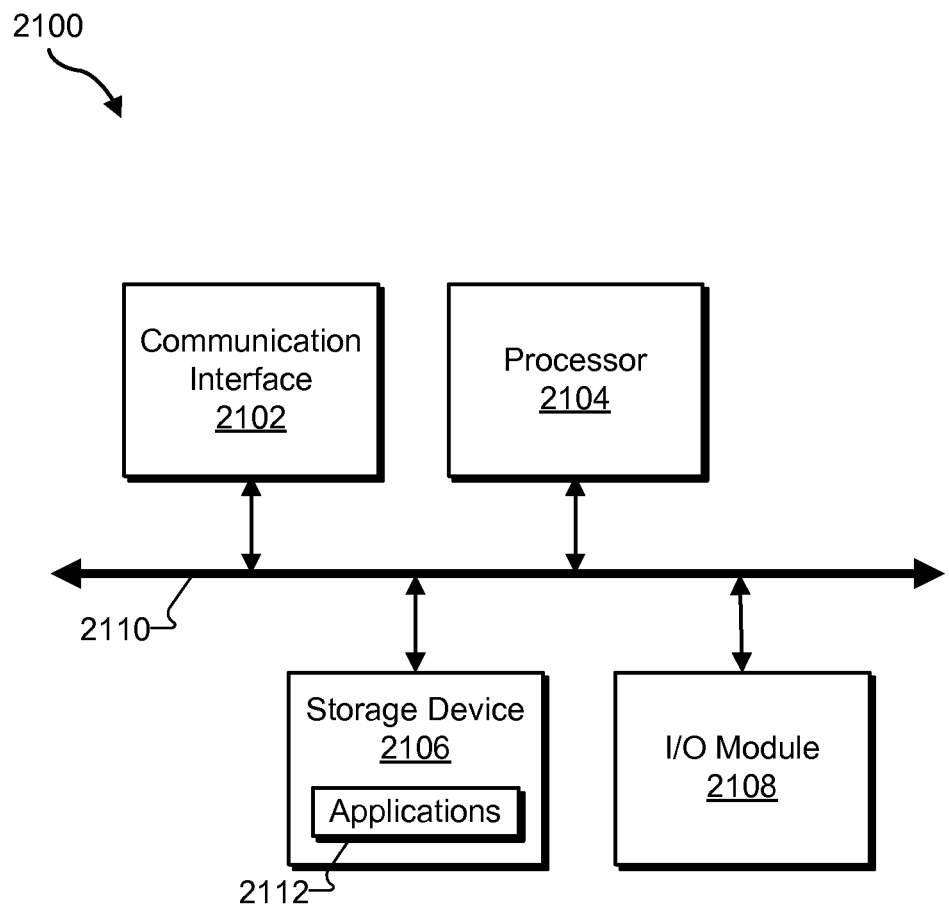
FIG. 21 illustrates an exemplary computing device according to principles described herein.

FIG. 21 illustrates an exemplary computing device 2100 that may be configured to perform one or more of the processes described herein. As shown in FIG. 21, computing device 2100 may include a communication interface 2102, a processor 2104, a storage device 2106, and an input/output ("I/O") module 2108 communicatively connected via a communication infrastructure 2110. While an exemplary computing device 2100 is shown in FIG. 21, the components illustrated in FIG. 21 are not intended to be limiting. Additional or alternative components may be used in other embodiments. Components of computing device 2100 shown in FIG. 21 will now be described in additional detail.

Communication interface 2102 may be configured to communicate with one or more computing devices. Examples of communication interface 2102 include, without limitation, a wired network interface (such as a network interface card), a wireless network interface (such as a wireless network interface card), a modem, an audio/video connection, and any other suitable interface.

Processor 2104 generally represents any type or form of processing unit capable of processing data or interpreting, executing, and/or directing execution of one or more of the instructions, processes, and/or operations described herein. Processor 2104 may direct execution of operations in accordance with one or more applications 2112 or other computer-executable instructions such as may be stored in storage device 2106 or another computer-readable medium.

Storage device 2106 may include one or more data storage media, devices, or configurations and may employ any type, form, and combination of data storage media and/or device. For example, storage device 2106 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 2106. For example, data representative of one or more executable applications 2112 configured to direct processor 2104 to perform any of the operations described herein may be stored within storage device 2106. In some examples, data may be arranged in one or more databases residing within storage device 2106.

I/O module 2108 may be configured to receive user input and provide user output and may include any hardware, firmware, software, or combination thereof supportive of input and output capabilities. For example, I/O module 2108 may include hardware and/or software for capturing user input, including, but not limited to, a keyboard or keypad, a touch screen component (e.g., touch screen display), a receiver (e.g., an RF or infrared receiver), and/or one or more input buttons.

I/O module 2108 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 2108 is configured to provide graphical data to a display for presentation to a user. The graphical data may be representative of one or more graphical user interfaces and/or any other graphical content as may serve a particular implementation.

In some examples, any of the systems and/or facilities described herein may be implemented by or within one or more components of computing device 2100. For example, one or more applications 2112 residing within storage device 2106 may be configured to direct processor 2104 to perform one or more processes or functions associated with chronic care management facility 302. Likewise, storage facility 304 may be implemented by or within storage device 2106.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
maintaining, by a chronic care solutions provider system, data representative of a chronic care plan for a patient with a chronic medical condition;
receiving, by the chronic care solutions provider system, data representative of a biometric reading acquired by a biometric device associated with the patient;
generating, by the chronic care solutions provider system, a plurality of actionable tasks based on the biometric reading and in accordance with the chronic care plan, the actionable tasks configured to assist the patient in managing the chronic medical condition;
concurrently presenting, by the chronic care solutions provider system within a patient portal accessible by the patient and displayed within a touch screen, a plurality of graphical task cards each representative of a distinct actionable task included in the plurality of actionable tasks, the concurrently presenting of the plurality of graphical task cards comprising presenting the graphical task cards in a staggered stack arrangement such that at least a portion of each of the graphical task cards is visible within the patient portal, wherein the graphical task cards are ordered within the staggered stack arrangement in accordance with an order in which the actionable tasks represented by the graphical task cards are to be completed by the patient;
detecting, by the chronic care solutions provider system while the graphical task cards are concurrently presented within the patient portal, a touching by the patient of the touch screen; and
shuffling, by the chronic care solutions provider system, the graphical task cards within the staggered stack arrangement in response to the touching of the touch screen by the patient, wherein the shuffling comprises graphically bringing a graphical task card included in the plurality of graphical task cards and located beneath a top of the staggered stack arrangement prior to the touching being performed to being located at the top of the staggered stack arrangement;
detecting, by the chronic care solutions provider system, a selection by the patient of the graphical task card;
and enlarging, by the chronic care solutions provider system, the selected graphical task card within the patient portal, wherein the enlarging comprises maximizing a size of the selected graphical task card within the patient portal such that a remaining number of graphical task cards included in the plurality of graphical task cards are not visible within the patient portal.

2. The method of claim 1, wherein each graphical task card included in the plurality of graphical task cards is interactive and configured to facilitate completion by the patient of a corresponding actionable task.

3. A method comprising:
maintaining, by a chronic care solutions provider system, data representative of a chronic care plan for a patient with a chronic medical condition;
receiving, by the chronic care solutions provider system, data representative of a biometric reading acquired by a biometric device associated with the patient;
generating, by the chronic care solutions provider system, a plurality of actionable tasks based on the biometric reading and in accordance with the chronic care plan, the actionable tasks configured to assist the patient in managing the chronic medical condition;
concurrently presenting, by the chronic care solutions provider system within a patient portal accessible by the patient, a plurality of graphical task cards each representative of a distinct actionable task included in the plurality of actionable tasks, the concurrently presenting of the plurality of graphical task cards comprising presenting the graphical task cards in a staggered stack arrangement such that at least a portion of each of the graphical task cards is visible within the patient portal, wherein the graphical task cards are ordered within the staggered stack arrangement in accordance with an order in which the actionable tasks represented by the graphical task cards are to be completed by the patient;
detecting, by the chronic care solutions provider system, a selection by the patient of a graphical task card included in the plurality of graphical task cards; and
enlarging, by the chronic care solutions provider system, the selected graphical task card within the patient portal, wherein the enlarging comprises maximizing a size of the selected graphical task card within the patient portal such that a remaining number of graphical task cards included in the plurality of graphical task cards are not visible within the patient portal.

4. The method of claim 1, further comprising:
detecting, by the chronic care solutions provider system, a selection by the patient of a graphical task card included in the plurality of graphical task cards, the graphical task card representative of an actionable task included in the plurality of actionable tasks; and
presenting, by the chronic care solutions provider system in response to the selection of the graphical task card and within the patient portal, content associated with the actionable task.

5. The method of claim 1, wherein the receiving of the data representative of the biometric reading acquired by the biometric device comprises receiving the data representative of the biometric reading from the biometric device by way of a cellular connection between the biometric device and a network interconnecting the biometric device and the chronic care solutions provider system.

6. The method of claim 1, wherein the receiving of the data representative of the biometric reading acquired by the biometric device comprises receiving the data representative of the biometric reading from a computing device associated with the patient.

7. The method of claim 1, further comprising:
maintaining, by the chronic care solutions provider system, data representative of a library of actionable tasks;
wherein the generating of the actionable tasks comprises using the biometric reading to automatically select the actionable tasks from the library of actionable tasks.

8. The method of claim 1, wherein the generating of the actionable tasks comprises:
presenting, within a practitioner portal accessible by a health care practitioner assigned to the patient, the biometric reading acquired by the biometric device;
receiving, by way of the practitioner portal, input provided by the health care practitioner in response to the presentation of the biometric reading; and
generating the actionable tasks based on the input provided by the health care practitioner.

9. The method of claim 1, wherein the generating of the actionable tasks is further based on one or more other biometric readings acquired by the biometric device prior to the biometric reading being acquired by the biometric device.

10. The method of claim 1, further comprising:
receiving, by the chronic care solutions provider system, data representative of an additional biometric reading associated with the patient acquired by an additional biometric device;
wherein the generating of the actionable tasks is further based on the additional biometric reading.

11. The method of claim 1, further comprising presenting, by the chronic care solutions provider system within the patient portal, at least one of information associated with the chronic care plan, social network content associated with the patient, and an advertisement associated with at least one of the chronic medical condition and the biometric reading.

12. The method of claim 1, further comprising presenting, by the chronic care solutions provider system within the patient portal, at least one of a graphical object representative of progress made by the patient towards one or more goals associated with the chronic care plan and at least one recommendation for managing the chronic medical condition.

13. A system comprising:
at least one physical computing device that comprises:
a storage facility that maintains data representative of a chronic care plan for a patient with a chronic medical condition; and
a chronic care management facility communicatively coupled to the storage facility and that
receives data representative of a biometric reading acquired by a biometric device associated with the patient,
determines that the biometric reading is outside an acceptable range specified in the chronic care plan,
generates a plurality of actionable tasks based on the biometric reading and in accordance with the chronic care plan, the actionable tasks configured to assist the patient in managing the chronic medical condition,
concurrently presents, within a patient portal accessible by the patient and displayed within a touch screen, a plurality of graphical task cards each representative of a distinct actionable task included in the plurality of actionable tasks by presenting the graphical task cards in a staggered stack arrangement such that at least a portion of each of the graphical task cards is visible within the patient portal, wherein the graphical task cards are ordered within the staggered stack arrangement in accordance with an order in which the actionable tasks represented by the graphical task cards are to be completed by the patient;
detects, while the graphical task cards are concurrently presented within the patient portal, a touching by the patient of the touch screen; and
shuffles the graphical task cards within the staggered stack arrangement in response to the touching of the touch screen by the patient, wherein the shuffling comprises graphically bringing a graphical task card included in the plurality of graphical task cards and located beneath a top of the staggered stack arrangement prior to the touching being performed to being located at the top of the staggered stack arrangement;
detects a selection by the patient of the graphical task card; and
enlarges, by the chronic care solutions provider system, the selected graphical task card within the patient portal, wherein the enlarging comprises maximizing a size of the selected graphical task card within the patient portal such that a remaining number of graphical task cards included in the plurality of graphical task cards are not visible within the patient portal.

14. A system comprising:
at least one physical computing device that comprises:
a storage facility that maintains data representative of a chronic care plan for a patient with a chronic medical condition; and
a chronic care management facility communicatively coupled to the storage facility and that
receives data representative of a biometric reading acquired by a biometric device associated with the patient,
generates a plurality of actionable tasks based on the biometric reading and in accordance with the chronic care plan, the actionable tasks configured to assist the patient in managing the chronic medical condition,
concurrently presents, within a patient portal accessible by the patient, a plurality of graphical task cards each representative of a distinct actionable task included in the plurality of actionable tasks, the concurrently presentation of the plurality of graphical task cards comprising presenting the graphical task cards in a staggered stack arrangement such that at least a portion of each of the graphical task cards is visible within the patient portal, wherein the graphical task cards are ordered within the staggered stack arrangement in accordance with an order in which the actionable tasks represented by the graphical task cards are to be completed by the patient,
detects a selection by the patient of a graphical task card included in the plurality of graphical task cards, and
enlarges the selected graphical task card within the patient portal by maximizing a size of the selected graphical task card within the patient portal such that a remaining number of graphical task cards included in the plurality of graphical task cards are not visible within the patient portal.

* * * * *